US012759976B2

(12) United States Patent
Huang et al.

(10) Patent No.: US 12,759,976 B2
(45) Date of Patent: Oct. 13, 2026

(54) PROCESSES FOR THE PREPARATION OF ALPHA-HYDROXY ESTERS BY ESTERIFICATION OF ALPHA-HYDROXY ACIDS

(71) Applicant: Kemin Industries, Inc., Des Moines, IA (US)

(72) Inventors: Shengshu Huang, Zhuhai City (CN); Fangyi Li, Tianjin City (CN); Li Xu, Xi'an City (CN); Filip Nuyens, Geel (BE); Ye Lao, West Des Moines, IA (US); Jatuporn Salaklang, Mol (BE); Zhuo Tang, Zhuhai City (CN)

(73) Assignee: Kemin Industries, Inc., Des Moines, IA (US)

( * ) Notice: Subject to any disclaimer, the term of this patent is extended or adjusted under 35 U.S.C. 154(b) by 970 days.

(21) Appl. No.: 17/640,431

(22) PCT Filed: Sep. 3, 2020

(86) PCT No.: PCT/US2020/049222
§ 371 (c)(1),
(2) Date: Mar. 4, 2022

(87) PCT Pub. No.: WO2021/046234
PCT Pub. Date: Mar. 11, 2021

(65) Prior Publication Data

US 2022/0332681 A1 Oct. 20, 2022

(30) Foreign Application Priority Data

Sep. 6, 2019 (WO) ................ PCT/CN2019/104692

(51) Int. Cl.
*C07C 319/20* (2006.01)
*A23K 50/10* (2016.01)
(Continued)

(52) U.S. Cl.
CPC ............ *C07C 319/20* (2013.01); *A23K 50/10* (2016.05); *C07C 319/30* (2013.01); *C07C 67/02* (2013.01)

(58) Field of Classification Search
None
See application file for complete search history.

(56) References Cited

U.S. PATENT DOCUMENTS 4,874,877 A 10/1989 Urban
5,705,675 A 1/1998 Blackburn et al.
(Continued)

FOREIGN PATENT DOCUMENTS

CN 102093271 A 6/2011
CN 109796384 A 5/2019
(Continued)

OTHER PUBLICATIONS

Clark ("Reactions of Acyl Chlorides with Alcohols", downloaded from https://chem.libretexts.org/Bookshelves/Organic_Chemistry/Supplemental_Modules_(Organic_Chemistry)/Acid_Halides/Reactions_of_Acid_Halides/Reactions_of_Acyl_Chlorides_with_Alcohols on May 20, 2025). (Year: 2025).*
(Continued)

*Primary Examiner* — Amy C Bonaparte
(74) *Attorney, Agent, or Firm* — McNeill PLLC

(57) ABSTRACT

The present disclosure provides processes for preparing an alpha-hydroxy ester from the corresponding alpha-hydroxy acid by transesterification. Also provided are alphahydroxy esters prepared according to processes disclosed herein and compositions comprising the alpha-hydroxy esters.

18 Claims, 9 Drawing Sheets

(51) Int. Cl.
*C07C 67/02* (2006.01)
*C07C 319/30* (2006.01)

(56) References Cited

U.S. PATENT DOCUMENTS

| | | | | |
|---|---|---|---|---|
| 6,479,695 | B1 * | 11/2002 | Garrait | C07C 319/20 562/581 |
| 6,660,880 | B2 | 12/2003 | Garrait et al. | |
| 9,809,528 | B2 | 11/2017 | Orazov et al. | |
| 2001/0029308 | A1 | 10/2001 | Garrait et al. | |
| 2005/0187293 | A1 | 8/2005 | Robert et al. | |
| 2006/0149090 | A1 | 7/2006 | Watanabe et al. | |
| 2008/0319043 | A1 | 12/2008 | Salman et al. | |
| 2009/0192328 | A1 * | 7/2009 | Hagiya | C07C 323/22 560/152 |
| 2016/0326182 | A1 | 11/2016 | Peltier et al. | |
| 2017/0369434 | A1 | 12/2017 | Mahoney et al. | |
| 2019/0016674 | A1 | 1/2019 | Zubiri et al. | |
| 2019/0016675 | A1 | 1/2019 | Mahoney et al. | |
| 2019/0119705 | A1 | 4/2019 | LLosa et al. | |

FOREIGN PATENT DOCUMENTS

| | | | |
|---|---|---|---|
| CO | 14119504 | | 8/2014 |
| EP | 0338735 | A1 | 10/1989 |
| EP | 1484311 | A1 | 12/2004 |
| JP | 02006467 | U | 1/1990 |
| JP | H06316557 | A | 11/1994 |
| WO | 0156980 | A1 | 8/2001 |
| WO | 2004008874 | A1 | 1/2004 |
| WO | 2008010609 | A1 | 1/2008 |
| WO | 2013068525 | A1 | 5/2013 |

OTHER PUBLICATIONS

CAS (2-Hydroxy-4-(methylthio)butanoic acid. CAS Common Chemistry. CAS, a division of the American Chemical Society, n.d. https://commonchemistry.cas.org/detail?cas_rn=583-91-5 (retrieved May 30, 2025) (CAS RN: 583-91-5)). (Year: 2025).*

Bolt ("Esters, Organic" Ullmann's Encyclopedia of Industrial Chemistry, first published Apr. 30, 2005, downloaded from https://onlinelibrary.wiley.com/doi/10.1002/14356007.a09_565.pub2# on May 30, 2025) (Year: 2005).*

Partial Supplementary European Search Report for EP Application No. 20861384.4, mailed Aug. 28, 2023, 13 pages.

Rehberg, C.E. et al., "Preparation of Methyl Acetoxypropionate", Industrial and Engineering Chemistry, 1944, vol. 36, No. 5, 469-472.

Walker, Louise F et al., "Synthesis of 2,5-dihydrofurans via alkylidene carbene insertion reactions", J. Chem. Soc., Perkin Trans 1, 2002, 965-981.

Noftsger, S. et al., "Determination of Rumen Degradability and Ruminal Effects of Three Sources of Methionine in Lactating Cows", J. Dairy Sci. 2005, 88:223-237.

Milewska, Maria J. et al., Synthesis of Schizokinen, Homoschizokinen, Its Imide and the Detection of Imide with 13C-N.M.R.-Spectroscopy, Journal f. prakt. Chemie. Band 329, Heft 3, 1987, 447-456.

Wang, Qun et al., "Effect of 2-hydroxy-4-(methylthio) butanoic acid isopropyl ester (HMBi) supplementation of diets with different protein levels on milk production and serum parameters in dairy cows", Journal of Nanjing Agricultural Univerisity, 2014, 37(3): 126-132, English Abstract.

Khan, Khalid Mohammed et al., "An expedient esterification of aromatic carboxylic acids using sodium bromate and sodium hydrogen sulfite", Tetrahedron, vol. 59, Issue 29, Jul. 14, 2003, pp. 5549-5554.

Wang, Min et al., "Reaction-controlled recovery of the copper (II) methanesulfonate catalyst for esterification", React Kinet Catal Lett 84, 223-228 (2005).

Houston et al., "Boric Acid Catalyzed Chemoselective Esterification of alpha-Hydroxycarboxylic Acids", Organic Letters, Feb. 11, 2004, vol. 6, p. 679-681.

International Search Report and Written Opinion from PCT/US2020/049222, mailed on Feb. 17, 2021, 15 pages.

Sprakel et al., "Solvent developments for liquid-liquid extraction of carboxylic acids in perspective", Separation and Purification Technology, Oct. 12, 2018, vol. 211, p. 935-957.

Katritzky, Alan R. et al., "Efficient Preparation of Aminoxyacyl Amides, Aminoxy Hybrid Peptides, and α-Aminoxy Peptides", J. Org. Chem. 2009, 74, 8690-8694.

Katritzky, Alan R. et al., "Efficient Preparation of Aminoxyacyl Amides, Aminoxy Hybrid Peptides, and α-Aminoxy Peptides", Supporting Information, J. Org. Chem. 2009, pp. 1-134.

St-Pierre, N.R. et al., "Effect of 2-Hydroxy-4-(Methylthio) Butanoic Acid (HMB) and Its Isopropyl Ester on Milk Production and Composition by Holstein Cows", J. Dairy Sci. 2005, 88: 2487-2497.

Studte, Christopher et al., "Zinc-Catalyzed Enantiospecific sp3-sp3 Cross Couping of α-Hydroxy Ester Triflates with Grignard Reagents", Supporting Information, Angew. Chem. Int. Ed. 2008, pp. 1-34.

Studte, Christopher et al., "Zinc-Catalyzed Enantiospecific sp3-sp3 Cross Couping of α-Hydroxy Ester Triflates with Grignard Reagents", Angew. Chem. Int. Ed. 2008, 47, 5451-5455.

Rulquin et al., "Effect of Different Forms of Methionine on Lactational Performance of Dairy Cows," J. Dairy Sci. 89:4387-4394 (2006).

Weng et al., "Chemoselective esterification of α-hydroxyacids catalyzed by salicylaldehyde through induced intramolecularity." RSC Advances 3(6):1976-1986 (2013).

* cited by examiner

PROCESSES FOR THE PREPARATION OF ALPHA-HYDROXY ESTERS BY ESTERIFICATION OF ALPHA-HYDROXY ACIDS

RELATED APPLICATIONS

This application is a national phase entry pursuant to 35 U.S.C § 371 of International Application No. PCT/US2020/049222, filed Sep. 3, 2020, which claims priority to International Application No. PCT/CN2019/104692 filed Sep. 6, 2019, which is incorporated by reference herein in its entirety for any purpose.

FIELD OF THE INVENTION

The present disclosure provides processes for preparing an alpha-hydroxy ester from the corresponding alpha-hydroxy acid by esterification, such as transesterification. Also provided are alpha-hydroxy esters prepared according to processes disclosed herein, compositions comprising the alpha-hydroxy esters, and methods of using the compositions.

BACKGROUND

Alpha-hydroxy ester analogs of natural amino acids are useful as dietary supplements and in the study of enzymatic processes and protein function. Synthesis of such esters typically employs acid-catalyzed Fischer esterification of the corresponding acid and an alcohol in the presence of a strong acid such as $H_2SO_4$ or Amberlyst® cationic exchange resin, acid-mediated hydrolysis of the corresponding nitrile in the presence of a strong acid, or enzyme-mediated processes. However, acid-catalyzed approaches lead to degradation of starting material and product and contamination of the product with dimeric and oligomeric components. Such methods typically provide low yields, and complex purification techniques are needed to isolate the target compound from the polymeric side-products. Enzymatic approaches require expensive and sensitive reagents and special reaction conditions.

An alpha-hydroxy ester of particular importance is isopropyl 2-hydroxy-4-(methylthio)butanoate (HMBi). HMBi is the isopropyl ester of the hydroxy analog of methionine, 2-hydroxy-4-(methylthio)butanoic acid (HMBA). HMBi is used to help supplement methionine in ruminants, including cows. Adequate methionine levels in dairy cows help maintain desired levels of milk protein synthesis and, in turn, desired levels of milk production. However, methionine content in the animal feedstock is vastly insufficient and has become a major limiting factor in the diet of the dairy cow. HMBi is a chemical derivative of methionine that readily and rapidly diffuses through the rumen wall, avoiding degradation by ruminal microbes. Once HMBi passes through the rumen wall, it is metabolized in the liver and becomes available for milk protein synthesis in dairy cows.

There is a need for additional processes for synthesizing alpha-hydroxy esters, such as HMBi, that employ inexpensive reagents and mild reaction conditions, and that provide the product esters in high yield and purity.

SUMMARY

In one aspect, the disclosure is directed to a method of preparing a compound of Formula (I):

(I)

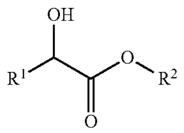

wherein $R^1$ is chosen from H; $C_{1-4}$ alkyl optionally substituted with —OH, —SH, —S—$C_{1-4}$ alkyl, —$CONH_2$, or guanidino; phenyl optionally substituted with —OH or $C_{1-4}$ alkyl; indolyl; and imidazolyl;

wherein $R^a$ and $R^b$ are each independently H or $C_{1-4}$ alkyl; and $R^2$ is $C_{1-8}$ alkyl or $C_{4-7}$ cycloalkyl;

comprising reacting a compound of Formula (II):

(II)

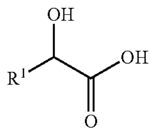

with a reagent of Formula (A) or Formula (B) or Formula (C):

(A)

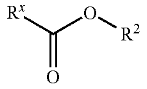

(B)

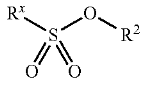

(C)

$(R^2O)_3B$ wherein $R^x$ is chosen from H, $C_{1-4}$ alkyl, and $CH_2$═CH—; and $R^y$ is $C_{1-3}$ alkyl.

In another aspect, the disclosure relates to a method of preparing a compound of Formula (I):

(I)

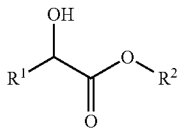

wherein $R^1$ is chosen from H; $C_{1-4}$ alkyl optionally substituted with —OH, —SH, —S—$C_{1-4}$ alkyl, —$CONH_2$, —$NR^aR^b$, or guanidino; phenyl optionally substituted with —OH or $C_{1-4}$ alkyl; indolyl; and imidazolyl;

wherein $R^a$ and $R^b$ are each independently H or $C_{1-4}$ alkyl; and $R^2$ is $C_{1-8}$ alkyl or $C_{4-7}$ cycloalkyl;

comprising reacting a compound of Formula (III):

(III)

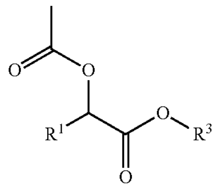

wherein $R^3$ is H or —C(O)$R^x$;

wherein $R^x$ is $C_{1-4}$alkyl.

with $R^2$—OH.

In another aspect, the disclosure relates to a method of preparing a compound of Formula (I-A):

(I-A)

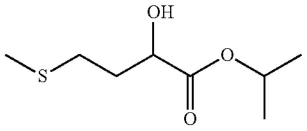

comprising:

(a) treating a compound of Formula (II-A):

(II-A)

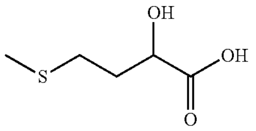

with acetyl chloride to provide a compound of Formula (III-A):

(III-A)

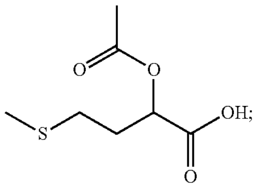

(b) reacting the compound of Formula (III-A) with isopropanol to provide a compound of Formula (IV-A):

(IV-A)

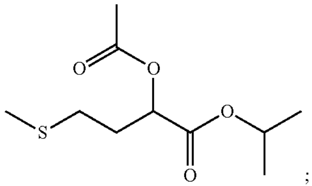

;

and (c) treating the compound of Formula (IV-A) with an aqueous base to provide the compound of Formula (I-A).

In another aspect, the disclosure relates to a method of preparing a compound of Formula (I-A):

(I-A)

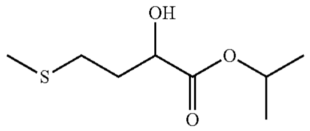

comprising:

(a) combining a compound of Formula (II-A):

(II-A)

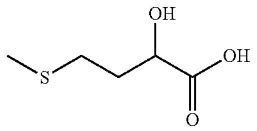

and n-heptane;

(b) drying the compound of Formula (II-A) by azeotropic distillation;

(c) adding n-heptane as a nonpolar solvent to the dried compound of Formula (II-A);

(d) treating the dried compound of Formula (II-A) in heptane with acetyl chloride to provide a compound of Formula (III-A):

(III-A1)

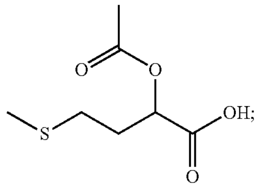

(e) reacting the compound of Formula (III-A1) with isopropanol in a two phase reaction mixture comprising a hydrophilic phase and a hydrophobic phase, to provide a compound of Formula (IV-A):

(IV-A)

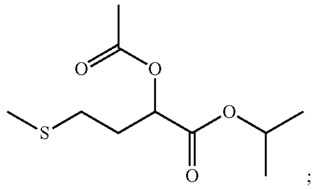

;

(f) treating the compound of Formula (IV-A) with an aqueous base to provide the compound of Formula (I-A) in the hydrophobic phase of the reaction mixture: and (g) separating the hydrophobic phase from the hydrophilic phase base to provide the compound of Formula (I-A).

In another aspect, the disclosure relates to a method of isolating the compound of Formula (I-A) (HMBi) by partitioning a mixture of HMBi and at least one impurity selected from HMBA, an HMBA dimer, an HMBA oligomer, an HMBi dimer, and an HMBi oligomer, between an n-heptane phase and a basic aqueous phase. In some embodiments, the mixture comprises HMBi and HMBA.

In another aspect, the disclosure relates to a method of isolating HMBi by partitioning a mixture of HMBi and at least one impurity chosen from HMBA, HMBA dimer, HMBA oligomer, HMBi dimer, and HMBi oligomer, between a hydrophobic phase and a hydrophilic phase during a two-phase reaction.

In another aspect, the disclosure is directed to a compound of Formula (I) or Formula (I-A) prepared as in any of the methods described herein.

In another aspect, the disclosure is directed to compound of Formula (I) or Formula (I-A), wherein the compound has a purity by weight (and/or by GC or by HPLC) of at least about 95%, or at least about 96%, or at least about 97%, or at least about 98%, and the compound is a crude compound, has not been purified, and/or has been purified only by fractional distillation.

In another aspect, the disclosure is directed to composition comprising at least about 95% by weight and/or by GC or HPLC analysis of the compound of Formula (I-A) and from about 1 to about 4999 ppm n-heptane as an impurity.

In another aspect, the disclosure is directed to an animal feed composition comprising a compound of Formula (I) or (I-A) as described herein.

In another aspect, the disclosure is directed to an animal feed composition comprising the compound of Formula (I) of Formula (I-A) as described herein. In some aspects, the animal feed is a cow feed, such as a dairy cow feed.

In another aspect, the disclosure is directed to a method of supplying bioavailable methionine to a dairy cow comprising administering to the cow a compound of Formula (I) or Formula (I-A) or an animal feed composition as described herein. In another aspect, the disclosure is directed to a method of supplying at least about 50% bioavailable methionine to a dairy cow comprising administering to the cow a compound of Formula (I) or Formula (I-A) or an animal feed composition as described herein. In another aspect, the disclosure is directed to a method of improving milk obtained from a dairy cow, comprising supplying to the cow a compound of Formula (I) or Formula (I-A) or an animal feed composition as described herein. In another aspect, the disclosure is directed to a method of improving the condition of a cow comprising supplying to the cow a compound of Formula (I) or Formula (I-A) or an animal feed composition as described herein.

DETAILED DESCRIPTION

Figure 1A:
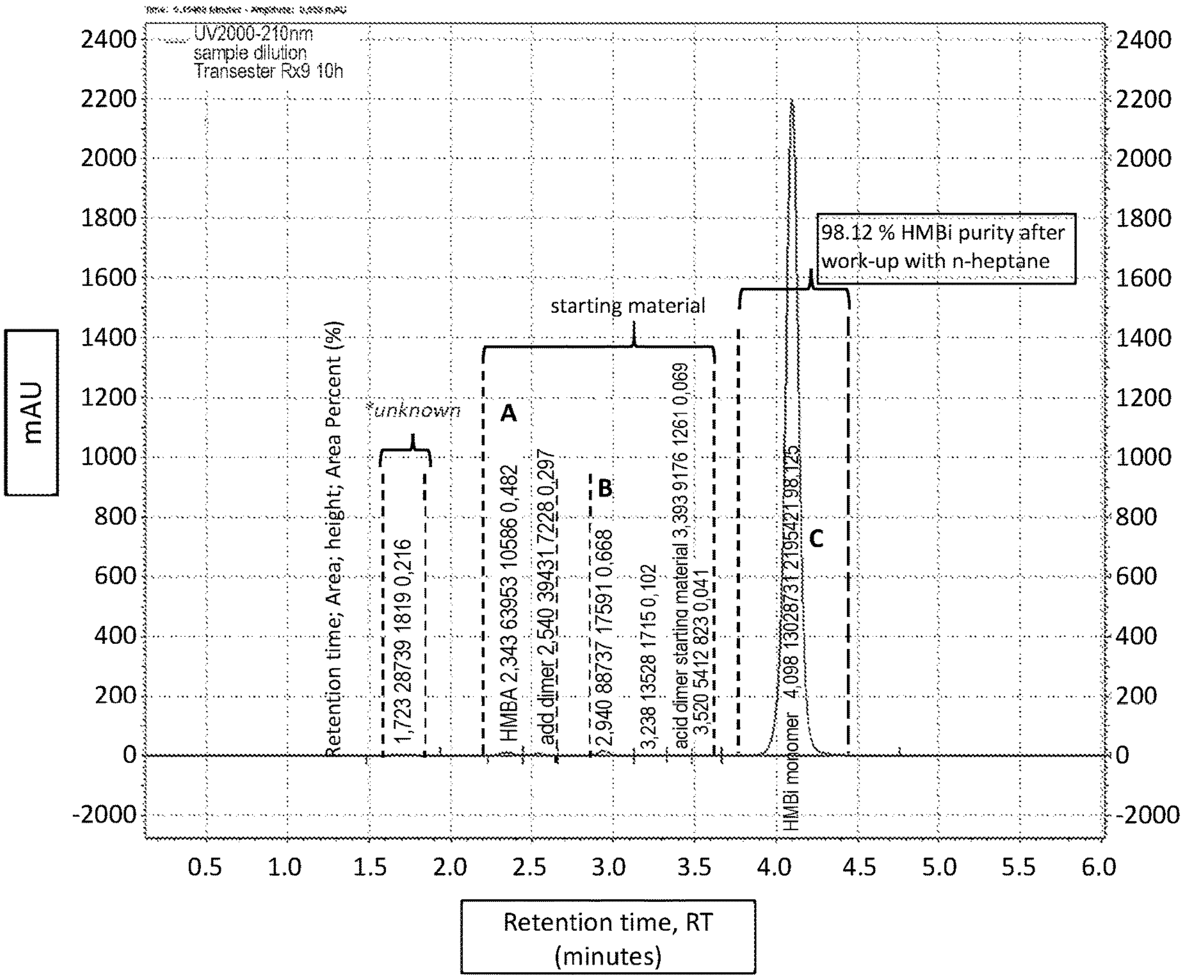
FIG. 1A is an HPLC chromatogram depicting the results of the reaction of HMBA and isopropyl acetate, in the presence of 5% aq. HCl, as described in Example 3.

Unless otherwise stated, the terms in this disclosure carry their plain and ordinary meaning as understood by those in the relevant art. The following terms used in the specification and claims are defined for the purposes of this disclosure and have the following meanings.

As used herein, the terms “isopropyl 2-hydroxy-4-(methylthio)butanoate,” “HMBi,” and “isopropyl ester of 2-hydroxy-4-(methylthio)butanoic acid” refer to a compound of the following structure (Formula I-A).

(I-A)

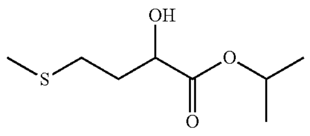

As used herein, the terms “2-hydroxy-4-(methylthio)butanoate,” “2-hydroxy-4-(methylthio)butanoic acid,” and “HMBA” refer to a compound of the following structure (Formula II-A).

(II-A)

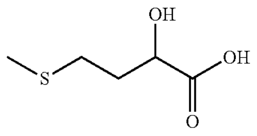

The compounds described herein may exist in racemic form, as a single enantiomer, or as a mixture of enantiomers. Thus, for example, HMBi refers to racemic HMBi (or “DL-HMBi”), or to D-HMBi or L-HMBi, or a mixture thereof.

Compounds described herein may also exist in salt forms. Chemical formulae shown herein should be understood to include the structures shown as well as salt forms thereof. For example, where a compound includes a carboxylic acid, the formula also encompasses salt forms of the conjugate base (carboxylate), such as sodium, potassium, magnesium, or calcium salts. Where a compound includes an indole or imidazole group, the formula also encompasses salt of the conjugate acids thereof, such as HCl salts.

"Alkyl" means a linear saturated monovalent hydrocarbon radical of one to eight carbon atoms (for example, one to six carbon atoms, one to four carbon atoms, or one to three carbon atoms) or a branched saturated monovalent hydrocarbon radical of three to eight carbon atoms (for example, three to six carbon atoms, three to four carbon atoms, or three carbon atoms), e.g., methyl, ethyl, propyl, isopropyl, butyl, isobutyl, sec-butyl, tert-butyl, pentyl (including all isomeric forms), and the like.

"Cycloalkyl" means a cyclic saturated monovalent hydrocarbon radical of three to ten carbon atoms, e.g., cyclopropyl, cyclobutyl, cyclopentyl, or cyclohexyl, and the like.

"Optional" or "optionally" means that the subsequently described event or circumstance may but need not occur, and that the description includes instances where the event or circumstance occurs and instances in which it does not. For example, an alkyl group "optionally substituted with —OH" means that the —OH may but need not be present, and the description includes situations where the alkyl group is substituted with an —OH group and situations where the alkyl group is not substituted with an —OH group.

The term "reaction solvent" refers to an organic liquid that is used to carry dissolved reactants. In some embodiments, one of the reagents of the reaction serves as a reagent and as the reaction solvent. In other embodiments, the reagents are diluted in a different reaction solvent.

The term "acid catalyst" refers to an acid added to a reaction in a sub-stoichiometric amount that serves to catalyze the reaction. An acid catalyst may be a Bronsted acid (such as an acid with a pKa of less than 7, such as HCl, $H_2SO_4$, $KHSO_4$, acetic acid, and the like) or a Lewis acid (such as boronic acid). In some embodiments, the acid is generated in situ, e.g., by reaction of acetyl chloride or TMSCl with water or an alcohol.

The term "strong acid" refers to an acid that dissociates completely into its component ions. Strong acids include, but are not limited to, HCl, $HNO_3$, $H_2SO_4$, HBr, HI, $HClO_4$, and $HClO_3$.

The term "concentration" refers to the amount of solute in a solvent. Herein, concentrations may be depicted by weight % or by molarity (M) or normality (N).

The term "reflux temperature" or "reflux" refers to the temperature at which a reaction solvent boils; typically, a condenser is used to cool the solvent vapor and condense it back into the reaction vessel. The precise temperature at which a given solvent reaches reflux may vary depending on environmental factors.

The term "heptane" or "n-heptane" refers to pure n-heptane, or n-heptane in a mixture with other C7 isomers (e.g., at least 90% n-heptane and at least 95% total C7 isomers).

The term "about" refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded.

The term "extract," "extraction," or "extracting," refers to a process of partitioning a material between an organic phase and an aqueous phase. In some aspects, the extracting is performed on a reaction mixture or a concentrated residue of a reaction mixture. An "extract" is the organic phase once separated from the aqueous phase. As used herein, extraction techniques can be used to isolate a final product. As used herein, extracting does not encompass purification methods performed on a crude reaction product, such as simple distillation, vacuum distillation, azeotropic distillation, fractional distillation, continuous distillation, flash chromatography, HPLC, or recrystallization.

As used herein, "purification" or "purifying" refers to a method of isolating the product of a reaction following completion of the reaction. Purification methods include simple distillation, vacuum distillation, azeotropic distillation, fractional distillation, continuous distillation, flash chromatography, HPLC, or recrystallization.

The term "substantially," e.g., "substantially in monomeric form" refers to the purity of a compound of Formula (I) or Formula (I-A), or to the purity of HMBA, relative to dimeric and/or oligomeric analogs.

As used herein, the term "dimer" or "dimeric compound" refers to a compound in which two molecules of a given monomer structure, or one molecule each of two different monomer structures, are condensed into a single molecule. In the case of HMBA, an HMBA dimer may exist, for example, in one of the following forms:

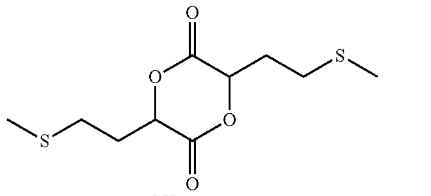

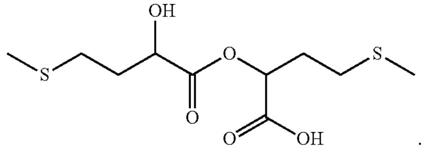

In the case of HMBA and HMBi, an HMBA/HMBi dimer (e.g., heterodimer) may exist, for example, in the following form:

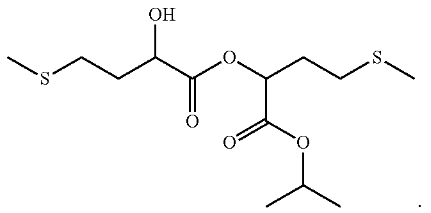

As used herein, the term "oligomer" or "oligomeric compound" refers to a compound in which more than two molecules of a given monomer structure, or more than two molecules of at least two different monomer structures, are condensed into a single polymeric structure. HMBA and HMBi may form homogeneous oligomers (e.g., HMBA trimer or tetramer) or heterogeneous HMBA/HMBi oligomers (comprising at least one HMBA monomer unit and at least one HMBi monomer unit). The "HMBA dimer" and "HMBA oligomer" structures are typically present in commercial samples of "88% HMBA" along with water.

The term "purity" or the expression of a percentage compound (e.g., x % HMBA) refers to the purity of a compound in a sample, as determined by weight, by GC analysis, and/or by HPLC analysis. In some aspects, the purity by weight is determined by GC or HPLC analysis with UV detection.

The term "purity by weight" refers to the purity of a compound in a sample with respect to other components in the sample, where the ratio of the mass of the compound to the mass of the sample is expressed as a percentage.

The term "purity" with reference to gas chromatography (GC) or HPLC purity means the calculated purity (expressed in %) of the peak area for the compound of interest relative to the sum of all the peak areas in the chromatogram. In some aspects, purity is determined by HPLC with UV detection.

In some aspects, purity is the purity required according to marketing regulations for a regulated product. In the case of HMBi, for example, the compound comprises 0.5% water or less (e.g., as determined by Karl-Fischer analysis). (See Commission Implementing Regulation (EU) No 469/2013 of 22 May 2013.)

The terms "crude," "crude product," and "crude compound" refer to the sample of a compound obtained from a reaction mixture after concentration of the reaction mixture and/or extraction of the reaction mixture into an organic solvent and concentration of the organic extract.

The term "not produced during the reaction" refers to a reaction that does not generate a given compound as a product. In some aspects, "not produced during the reaction" means not produced in stoichiometric amounts, or in catalytic amounts, or in detectable amounts. In some aspects, "not produced during the reaction" means the material may be present at the beginning of the reaction (e.g., in a mixture with a starting material) but the amount of the material does not increase substantially during the reaction. In some aspects, isopropyl alcohol and/or water are not produced in certain reactions described herein. Detection of isopropyl alcohol can be done by GC or other methods known in the art, and detection of water can be done by Karl Fischer analysis or other methods known in the art.

As used herein, the term "reducing the amount of water" refers to partial or complete removal of water from the reaction mixture. Complete removal of water indicates water is not detectable using standard detection methods, such as Karl-Fischer analysis.

The term "animal feed composition" refers to a product suitable for use in animal nutrition. In some aspects, the animal feed composition is an animal feed (e.g., food or drinking water comprising the supplement), and in some aspects, the animal feed composition is a feed additive. The feed additive is suitable for mixing with animal feedstuff or with drinking water.

The term "carrier" refers to a suitable carrier for an animal feed additive. Suitable carriers include water (for a liquid or solid feed additive) or silica (for a solid feed additive). In some aspects, the carrier is silica (silicon dioxide). In some aspects, the feed additive comprises the compound and silica in a 3:2 ratio.

In some aspects, an animal feed comprises a pelleted, protein-rich feed (e.g., based on groundnuts, rape seed meal, and/or soybean meal) supplemented with 2.5% or 1% HMBi by weight. In some aspects, an animal feed comprises about 45% and about 50% cereal (maize, barley, wheat, and/or wheat by-products), supplemented with 0.5% or 3.0% HMBi by weight. In some aspects, an animal feed comprises a mash feed with molasses, or a pelleted feed, each supplemented with 2.5% or 1% HMBi by weight.

The term "administering" refers to providing the supplement to the target animal. Administering may be done orally, e.g., through ingestion of food or drinking water comprising the compound, or by injection or other mode of administration.

As used herein, "improving milk" refers to an improvement in the quality and/or quantity of milk produced by a treated cow or a group of treated cows as compared to that produced by untreated counterparts. Improvements in milk include, for example, increased protein content in the milk (e.g., increase in alpha, beta, and/or kappa proteins), increased fat content in the milk, and/or increased volume of milk produced.

As used herein, "improving the condition of a cow" refers to an improvement in a health measure of treated cow or group of treated cows as compared to the health measure in untreated counterparts. Improvement of the condition of a cow can refer to, for example, an increase in some characteristic relative to untreated animal; e.g., weight gain.

As used herein, an improvement in fertility includes, for example, shortening the interval between calving and reproduction and/or increasing the percentage fertilization during insemination.

As used herein, an improvement in liver function includes, for example, reduction in metabolic problems, improvement in levels of very low-density lipoproteins, reduction in blood ketosis, and/or reduction in the incidence of hepatic steatosis.

As used herein, "increase in energy" refers to, for example, stimulation of fermentation processes in the rumen, resulting in an increase in digestible organic matter, and therefore more energy for the animal.

Transesterification

In some embodiments, the disclosure relates to method of preparing a compound of Formula (I):

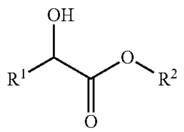

(I)

wherein $R^1$ is chosen from H; $C_{1-4}$ alkyl optionally substituted with —OH, —SH, —S—$C_{1-4}$ alkyl, —$CONH_2$, or guanidino; phenyl optionally substituted with —OH or $C_{1-4}$ alkyl; indolyl; and imidazolyl;

wherein $R^a$ and $R^b$ are each independently H or $C_{1-4}$ alkyl; and $R^2$ is $C_{1-8}$ alkyl or $C_{4-7}$ cycloalkyl;

comprising reacting a compound of Formula (II):

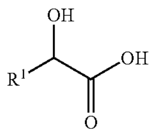

(II)

with a reagent of Formula (A) or Formula (B) or Formula (C):

(A)

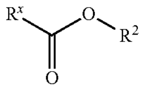

(B)

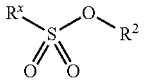

(C)

$(R^2O)_3B$ wherein $R^x$ is chosen from H, $C_{1-4}$ alkyl, and $CH_2{=}CH—$; and $R^y$ is $C_{1-3}$ alkyl.

In some embodiments, the reagent of Formula (A) (e.g., isopropyl acetate, isopropyl formate, isopropyl acrylate) or Formula (B) (e.g., isopropyl methanesulfonate) or Formula (C) (e.g., triisopropyl borate) serves as the reaction solvent. In some embodiments, the reagent of Formula (A), (B), or (C) is used in an amount of from about 1 molar equivalent ("equivalent" or "eq." or "equiv.") to about 20 equivalents, or from about 1 equivalent to about 10 equivalents, or from about 1 equivalent to about 5 equivalents, or from about 1 equivalent to about 3 equivalents, relative to the HMBA starting material. In some embodiments, the reagent of Formula (A) is isopropyl acetate and isopropyl acetate serves as the reaction solvent (i.e., neat isopropyl acetate, without added solvent). In some embodiments, the reagent of Formula (B) is isopropyl methanesulfonate and isopropyl methanesulfonate serves as the reaction solvent. In some embodiments, the reagent of Formula (C) is triisopropyl borate and triisopropyl borate serves as the reaction solvent. In some embodiments, the reaction is performed in at least one separate organic solvent that is not the reagent of Formula (A), (B), or (C). In some embodiments, the at least one separate organic solvent is $R^2$—OH (e.g., methanol, ethanol, isopropyl alcohol, and the like), diisopropyl ether, THF, dichloromethane, methyl-THF, toluene, and dioxolane. In some embodiments, the reaction solvent is isopropyl alcohol. In some embodiments, the reaction solvent is isopropyl alcohol, the reagent is the reagent of Formula (A) (e.g., isopropyl acetate), and from about 1 equivalent to about 10 equivalents, or from about 1 equivalent to about 5 equivalents, or from about 1 equivalent to about 3 equivalents, of the reagent is used relative to the HMBA starting material.

In some embodiments, the reagent is the reagent of Formula (A), such as isopropyl acetate, and the reagent is produced in situ by reacting a compound of formula $R^xC(O)Cl$, such as acetyl chloride, with a compound of formula $R^2OH$, such as isopropyl alcohol. The resulting mixture of the reagent of Formula (A), such as isopropyl acetate, is combined with the compound of Formula (II) or (II-A) for the reacting.

In some embodiments, $R^1$ is H. In some embodiments, $R^1$ is $C_{1-4}$ alkyl optionally substituted with —OH, —SH, —S—$C_{1-4}$ alkyl, —$CONH_2$, —$NR^aR^b$, or guanidino. In some embodiments, $R^1$ is $C_{1-4}$ alkyl optionally substituted with —OH, —SH, or —S—$C_{1-4}$ alkyl. In some embodiments, $R^1$ is chosen from methyl, ethyl, isopropyl, isobutyl, sec-butyl, —$CH_2$—OH, and —$CH_2CH_2$—S—$C_{1-4}$ alkyl. In some embodiments, $R^1$ is —$CH_2CH_2$—S—$CH_3$. In some embodiments, $R^1$ is chosen from phenyl optionally substituted with —OH or $C_{1-4}$ alkyl; indolyl; and imidazolyl.

In some embodiments, $R^2$ is chosen from methyl, ethyl, and isopropyl. In some embodiments, $R^2$ is isopropyl.

In some embodiments, the reagent is the reagent of Formula (A). In some embodiments, $R^x$ is chosen from H, methyl, and $CH_2{=}CH—$. In some embodiments, $R^x$ is methyl. In some embodiments, the reagent is the reagent of Formula (B). In some embodiments, $R^y$ is methyl. In some embodiments, the reagent is the reagent of Formula (C). In some embodiments, the reagent is the reagent of Formula (C) and $R^2$ is isopropyl.

In some embodiments, $R^1$ is —$CH_2CH_2$—S—$CH_3$ and $R^2$ is isopropyl. In some embodiments, $R^1$ is —$CH_2CH_2$—S—$CH_3$, $R^2$ is isopropyl, the reagent is the reagent of Formula (A), and $R^x$ is methyl. In some embodiments, $R^1$ is —$CH_2CH_2$—S—$CH_3$ and $R^2$ is isopropyl. In some embodiments, $R^1$ is —$CH_2CH_2$—S—$CH_3$, $R^2$ is isopropyl, the reagent is the reagent of Formula (B), and $R^y$ is methyl.

In some embodiments, the disclosure relates to a method of preparing a compound of Formula (I-A):

(I-A)

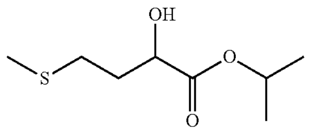

comprising reacting a compound of Formula (II-A):

(II-A)

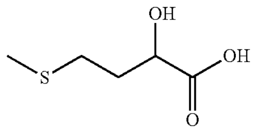

with isopropyl acetate or isopropyl methanesulfonate. In some embodiments, the reacting is with isopropyl acetate. In some embodiments, the reacting is with isopropyl acetate in isopropyl alcohol as the reaction solvent.

In some embodiments, the methods of preparing compounds of Formula (I) and (I-A) disclosed herein further comprise adding at least one nonpolar solvent to the reaction mixture, for example the reaction between the compound of Formula (II) and Formula (A), (B), or (C); or the reaction between the compound of Formula (II-A) and isopropyl acetate or isopropyl methanesulfonate. In some embodiments, the reaction is a two-phase reaction comprising a hydrophobic phase and a hydrophilic phase of a reaction mixture. In some embodiments, the nonpolar solvent is chosen from petroleum ether, toluene, methyl tert-butyl ether, hexane, cyclohexane, hexanes, n-heptane, octane, nonane, decane and benzene. In some embodiments, the nonpolar solvent is chosen from hexane, hexanes, n-heptane, octane, nonane, decane, benzene, toluene and methyl tert-butyl ether. In some embodiments, the nonpolar solvent is n-heptane.

In some embodiments, the reacting is performed in the absence of an acid catalyst. In some embodiments, the reacting is performed in the presence of at least one acid catalyst. In some embodiments, the at least one acid catalyst is chosen from $H_2SO_4$, HCl, and p-toluenesulfonic acid (p-TsOH). In some embodiments, the at least one acid catalyst is HCl. In some embodiments, the acid catalyst is HClthat is generated in situ by reaction of acetyl chloride or TMSCl with water or an alcohol (e.g., Formula (II) or (II-A). In some embodiments, the reacting is performed at a pH of about 1 or greater. In some embodiments, the reacting is performed at a pH of about 3 or greater.

In some embodiments, the compound of Formula (II) or Formula (II-A) (starting material) is present in a sample comprising water prior to the reacting, and the method further comprises reducing the amount of water in the sample by contacting the sample with an acid chloride of Formula (D):

$C_{1-3}$ alkyl—C(O)Cl (D)

to generate a catalyst mixture comprising HCl and combining the reagent with the catalyst mixture. In some embodiments, at least a molar equivalent, or a molar excess, of the acid chloride of Formula (D) is used relative to the amount of water in the sample (as determined, for example, by Karl-Fischer analysis). In some embodiments, the HCl is thereby generated in situ.

In some embodiments, the compound of Formula (II) or Formula (II-A) (starting material) is present in a sample comprising water prior to the reacting, and the method comprises treating the sample with at least one drying agent prior to the reacting. In some embodiments, the at least one drying agent is chosen from $MgSO_4$, $Na_2SO_4$, $PO_5$, diatomaceous earth, $CaCl_2$, molecular sieves, or an azeotrope solvent (e.g., a solvent such as n-propanol or benzene). In some embodiments, the at least one drying agent is chosen from $MgSO_4$ and $Na_2SO_4$. In some embodiments, the drying agent is added neat to the sample. In other embodiments, the sample is diluted in a polar or nonpolar solvent, such as diethyl ether, ethyl acetate, or dichloromethane, and is dried over the drying agent. In some embodiments, the drying agent is removed from the sample by filtration. In other embodiments, the drying agent is an azeotrope solvent and is removed by distillation (e.g., azeotropic removal of water). In some embodiments, the azeotrope solvent is chosen from hexane, n-heptane, n-propanol, isopropyl acetate, ethyl acetate, toluene and benzene.

In some embodiments, the reacting provides a reaction mixture comprising the compound of Formula (I) or Formula (I-A), and the method further comprises reducing the amount of the reagent of Formula (A) (such as isopropyl acetate), or Formula (B) (such as isopropyl methanesulfonate), or Formula (C) (such as triisopropyl borate), optionally by distillation, to provide a crude residue. In some embodiments, the method further comprises adding base to the reaction mixture or the crude residue, optionally where the base is sodium acetate, aqueous NaOH, such as 0.1 to 10 N aqueous NaOH, or 5 N NaOH, aqueous $NaHCO_3$, aqueous $K_2CO_3$, or aqueous $Na_3PO_4$, preferably where the base is 0.1 to 10 N aqueous NaOH, or 5 N NaOH, to increase the pH to a range of from about 5 to about 10, or about 5 to about 9, or about 5 to about 8 to provide a basic mixture, and extracting the compound of Formula (I) or Formula (I-A) from the basic mixture into at least one nonpolar solvent to provide an extract. In some embodiments, the at least one nonpolar solvent is chosen from hexane, hexanes, n-heptane, octane, nonane, and decane. In some embodiments, the at least one nonpolar solvent is n-heptane. In some embodiments, the volume of n-heptane used for the extracting is about 1 to 10 mL, or about 1 to 5 mL, or about 1 to 3 mL, or about 2 mL per kilogram of the calculated HMBi yield or the mass of the crude residue (e.g., the calculated or estimated amount of HMBi in the mixture). In some embodiments, the n-heptane used for the extracting is at a temperature of from about 25° C. to 50° C., or from about 30° C. to about 50° C., from about 30° C. to about 40° C., before the extracting. In some embodiments, the extract comprises the compound of Formula (I) or Formula (I-A) in at least about 95% purity by GC, by HPLC, or by weight. In some embodiments, the method comprises removing the at least one nonpolar solvent from the extract, optionally by distillation, to provide the compound of Formula (I) or Formula (I-A) in at least about 95% purity by GC, by HPLC, or by weight.

In some embodiments, the reacting provides a reaction mixture comprising the compound of Formula (I) or Formula (I-A), and the method further comprises adding base to the reaction mixture, optionally where the base is solid sodium acetate, to increase the pH to a range of from about 5 to about 10, or about 5 to about 9, or about 5 to about 8 to provide a basic mixture, drying the basic mixture using a drying agent to provide a dried basic mixture, and purifying the compound of Formula (I) or Formula (I-A) from the dried basic mixture by distillation to provide the compound of Formula (I) or Formula (I-A) in at least about 95% purity by GC, by HPLC, or by weight.

In some embodiments, $R^2$—OH, e.g., isopropyl alcohol, is not produced during the reacting. In some embodiments, water is not produced during the reacting.

In some embodiments, the reacting is performed at a temperature of at least about 20° C., or at least about 30° C., or at least about 40° C., or at least about 50° C., or at least about 60° C., or at least about 70° C., or at least about 80° C., or at least about 90° C., or at a temperature ranging from about 20° C. to about 150° C., or from about 20° C. to about 100° C., or from about 20° C. to about 90° C., or from about 60° C. to about 150° C., or from about 60° C. to about 100° C., or from about 60° C. to about 95° C., or from about 75° C. to about 90° C., or from about 80° C. to about 150° C., or from about 80° C. to about 100° C., or from about 80° C. to about 90° C., or at a temperature of about 89° C., or at the reflux temperature of the reagent of Formula (A) or Formula (B). In some embodiments, wherein the reagent is the reagent of Formula (A) and the reacting is performed at a temperature of at least about 60° C., or at least 75° C., or at about 80° C., or at least about 90° C., or at least about 100° C., or at a range from about 60° C. to about 150° C., or from about 60° C. to about 100° C., or from about 60° C. to about 95° C., or from about 75° C. to about 90° C., or from about 80° C. to about 150° C., or from about 80° C. to about 100° C., or from about 80° C. to about 90° C., or at the reflux temperature of the reagent of Formula (A); or wherein the reagent is the reagent of Formula (B) and the reacting is performed at a temperature from about 20° C. to about 90° C., or about 20° C. to about 60° C., or about 20° C. to about 30° C.

In some embodiments, the reacting is performed for a time ranging from about 1 hour to about 24 hours, or from about 2 hours to about 15 hours, or from about 3 hours to about 14 hours, or from about 4 hours to about 12 hours, of from about 4 hours to about 10 hours, or from about 10 to about 20 hours, or from about 14 to about 16 hours.

In some embodiments, following the reacting, the compound of Formula (I) or Formula (I-A) is extracted using at least one suitable solvent such as: petroleum ether, toluene, methyl tert-butyl ether, hexane, cyclohexane, hexanes, n-heptane, octane, nonane, decane and benzene. In some embodiments, following the reacting, the compound of Formula (I) or Formula (I-A) is extracted using at least one suitable solvent such as: hexane, hexanes, n-heptane, octane, nonane, decane, benzene, toluene or methyl tert-butyl ether. In some embodiments, before reacting the compound of Formula (I) or Formula (I-A), at least one suitable solvent, such as n-heptane or toluene, is added to the reaction mixture. In some embodiments, the solvent is a nonpolar solvent. In some embodiments, the solvent is an apolar solvent. In some embodiments, the solvent is hexane, hexanes, n-heptane, octane, nonane, or decane, or a mixture of isomers thereof. In some embodiments, the solvent is n-heptane. In some embodiments, following the reacting, the compound of Formula (I) or Formula (I-A) is extracted into n-heptane. In some embodiments, the n-heptane extraction occurs immediately after reaction in the reaction vessel. In some embodiments, the reaction is a two-phase reaction and the n-heptane extraction occurs upon formation of the compound of Formula (I) during the reaction in the reaction vessel. In some embodiments, the reaction mixture is adjusted to a pH of from about 5 to about 10, or about 5 to about 9, or about 5 to about 8 and the resulting mixture is extracted with n-heptane. In some embodiments, the reaction is a two-phase reaction and the reaction mixture is adjusted to a pH of from about 5 to about 10, or about 5 to about 9, or about 5 to about 8 thereby increasing the amount of compound of Formula (I) that partitions into the n-heptane. In some embodiments, the volume of n-heptane is about 1 to 10 mL, or about 1 to 5 mL, or about 1 to 3 mL, or about 2 mL per kilogram of the calculated HMBi yield or the mass of the crude residue (e.g., the calculated or estimated amount of HMBi present in the mixture). In some embodiments, the extracting is done with n-heptane that is at a temperature of from about 25° C. to 50° C., or from about 30° C. to about 50° C., from about 30° C. to about 40° C., before the extracting. In some embodiments, n-heptane selectively extracts HMBi over HMBA or HMBA and/or HMBi dimer or oligomer materials.

In some embodiments, the method further comprises combining isopropyl alcohol with acetyl chloride to produce a solution of isopropyl acetate in isopropanol in isopropanol and the reacting of the compound of Formula (II) or Formula (II-A) with the reagent of Formula (A), wherein the reagent of Formula (A) is isopropyl acetate, comprises adding the compound of Formula (II) or Formula (II-A) to the solution of isopropyl acetate in isopropanol.

Esterification via Stoichiometric Acetylation

In one aspect, the present disclosure relates to a method of preparing a compound of Formula (I):

(I)

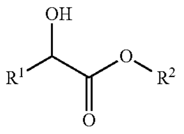

wherein $R^1$ is chosen from H; $C_{1-4}$ alkyl optionally substituted with —OH, —SH, —S—$C_{1-4}$ alkyl, —$CONH_2$, —$NR^aR^b$, or guanidino; phenyl optionally substituted with —OH or $C_{1-4}$ alkyl; indolyl; and imidazolyl;

wherein $R^a$ and $R^b$ are each independently H or $C_{1-4}$ alkyl; and $R^2$ is $C_{1-8}$ alkyl or $C_{4-7}$ cycloalkyl;

comprising reacting a compound of Formula (III-A) or Formula (III-B):

(III-A)

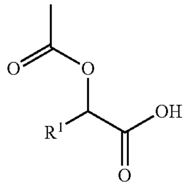

(III-B)

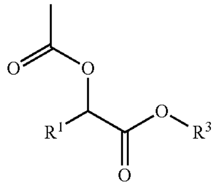

wherein $R^3$ is —$C(O)R^x$;

wherein $R^x$ is $C_{1-4}$alkyl.

with $R^2$—OH.

In some embodiments, $R^2$—OH is the solvent for the reacting of the compound of Formula (III-A) or (III-B).

In some embodiments, $R^1$ is H. In some embodiments, $R^1$ is $C_{1-4}$ alkyl optionally substituted with —OH, —SH, —S—$C_{1-4}$alkyl, —$CONH_2$, —$NR^aR^b$, or guanidino. In some embodiments, $R^1$ is $C_{1-4}$alkyl optionally substituted with —OH, —SH, or —S—$C_{1-4}$ alkyl. In some embodiments, $R^1$ is chosen methyl, ethyl, isopropyl, isobutyl, sec-butyl, —$CH_2$—OH, and —$CH_2CH_2$—S—$C_{1-4}$ alkyl. In some embodiments, $R^1$ is —$CH_2CH_2$—S—$CH_3$. In some embodiments, $R^1$ is chosen from phenyl optionally substituted with —OH or $C_{1-4}$ alkyl; indolyl; and imidazolyl.

In some embodiments, $R^2$ is methyl, ethyl, or isopropyl. In some embodiments, $R^2$ is isopropyl.

In some embodiments, the method comprises reacting the compound of Formula (III-A) with $R^2$—OH. In some embodiments, the method comprises reacting the compound of Formula (III-B) with $R^2$—OH.

In some embodiments, the reacting with $R^2$—OH is performed at a temperature of at least about 20° C., or at least about 30° C., or at least about 40° C., or at least about 50° C., or at least about 60° C., or at least about 70° C., or at least about 80° C., or at a temperature ranging from about 20° C. to about 90° C., or from about 60° C. to about 95° C., or from about 75° C. to about 90° C., at about 82° C., or at the reflux temperature of $R^2$—OH. In some embodiments, the reacting is performed for a time ranging from about 1 hour to about 24 hours, or from about 2 hours to about 15 hours, or from about 3 hours to about 14 hours, or about 4 hours to about 12 hours.

In some embodiments, the disclosure relates to reacting a compound of Formula (III-A) or a compound of Formula (III-B) with $R^2$—OH, wherein $R^1$ and $R^2$ are as defined herein, to provide a compound of Formula (IV):

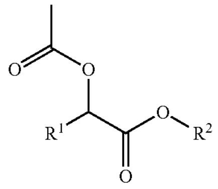

(IV)

wherein $R^1$ and $R^2$ are defined herein. In some embodiments, the method of preparing a compound of Formula (I) comprises reacting the compound of Formula (III-A) or Formula (III-B) with $R^2$—OH, to provide a compound of Formula (IV) in a Formula (IV) reaction mixture;

and reacting further comprises treating the compound of Formula (IV) with an aqueous base to provide the compound of Formula (I).

In some embodiments, the method further comprises:

(a) concentrating the Formula (IV) reaction mixture to form a concentrated reaction mixture; or (b) extracting the compound of Formula (IV) from the Formula (IV) reaction mixture into an organic solvent to form an extract and concentrating the extract to form a concentrated extract;

wherein treating the compound of Formula (IV) in the concentrated reaction mixture or the concentrated extract with an aqueous base comprises treating the Formula (IV) concentrate with the aqueous base.

In some embodiments, the method of reacting a compound of Formula (III-A) or a compound of Formula (III-B) with $R^2$—OH to provide a compound of Formula (IV) further comprises adding at least one nonpolar solvent to the reaction between the compound of Formula (III-A) or Formula (III-B) and $R^2$—OH. In some embodiments, the method is a two-phase reaction comprising a hydrophobic phase and a hydrophilic phase of a reaction mixture. In some embodiments, the nonpolar solvent is chosen from petroleum ether, toluene, methyl tert-butyl ether, hexane, cyclohexane, hexanes, n-heptane, octane, nonane, decane and benzene. In some embodiments, the nonpolar solvent is chosen from hexane, hexanes, n-heptane, octane, nonane, decane, benzene, toluene and methyl tert-butyl ether. In some embodiments, the nonpolar solvent is n-heptane.

In some embodiments, the compound of Formula (I) partitions into the hydrophobic phase of the reaction mixture.

In some embodiments, the method of preparing a compound of Formula (I) further comprises, after the treating the compound of Formula (IV) with the aqueous base to provide the compound of Formula (I) in the hydrophobic phase of the reaction mixture, separating the hydrophobic phase and the hydrophilic phase of the reaction mixture and concentrating the Formula (I) in the hydrophobic phase to provide the compound of Formula (I).

In some embodiments, the aqueous base is aqueous NaOH, such as 0.1 N NaOH, aqueous $NaHCO_3$, aqueous $K_2CO_3$, or aqueous $Na_3PO_4$. In some embodiments, the aqueous base is aqueous NaOH, such as 0.1 N NaOH, or aqueous $NaHCO_3$.

In some embodiments, the method further comprises, after the treating the compound of Formula (IV) with the aqueous base to provide the compound of Formula (I), extracting the compound of Formula (I) into an organic solvent to form a Formula (I) extract, and concentrating the Formula (I) extract to provide the compound of Formula (I). In some embodiments, the treating with aqueous base was performed at a temperature of at least about 0° C., or at least about 20° C., or at least about 25° C., or at least about 30° C., or at least about 40° C., or at a temperature of from about 0° C. to about 70° C., or from about 20° C. to about 50° C., or from about 20° C. to about 30° C. In some embodiments, the treating with aqueous base was performed for a time ranging from about 1 hour to about 24 hours, or from about 1 hour to about 5 hours, or from about 1 hour to about 3 hours.

In some embodiments, the method of preparing a compound of Formula (I) comprises treating a compound of Formula (II):

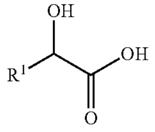

(II)

with an acylating agent to provide the compound of Formula (III-A) or Formula (III-B). In some embodiments, the acylating agent is acetyl chloride or acetic anhydride.

In some embodiments, the method further comprises, prior to reacting the compound of Formula (II) with an acylating agent, first adding a drying agent to the compound Formula (II), followed by drying the compound of Formula (II). In some embodiments, the at least one drying agent is an azeotrope solvent. In some embodiments, the at least one drying agent is n-heptane.

In some embodiments, the acylating agent is acetyl chloride, optionally wherein acetyl chloride is the reaction solvent.

In some embodiments, the method comprises reacting the compound of Formula (III-A) with $R^2$—OH, and the acylating agent is present in an amount ranging from about 1.0 to about 1.5 molar equivalents, or from about 1.0 to about 1.2 molar equivalents, or in an amount of about 1.0, 1.05, 1.1, or 1.2 molar equivalents relative to the compound of Formula (II). In some embodiments, the method comprises reacting the compound of Formula (III-B) with $R^2$—OH, and the acylating agent is present in an amount ranging from about 1.9 to about 2.5 molar equivalents, or from about 1.9 to about 2.1 molar equivalents, or in an amount of about 2.0 molar equivalents, relative to the compound of Formula (II).

In some embodiments, the treating of the compound of Formula (II) with the acylating agent comprises adding the acylating agent to the compound of Formula (II) at a temperature ranging from about 0° C. to about 20° C. to form an acylating mixture, and warming the acylating mixture to a temperature ranging from about 21° C. to about 80° C., or from about 40° C. to about 80° C., or about 52° C., or the reflux temperature of the acylating agent. In some embodiments, the acylating agent is acetyl chloride, and the warming comprises warming the acylating mixture to the reflux temperature of acetyl chloride, or to about 52° C.

In some embodiments, the method provides the compound of Formula (I) as a crude compound of Formula (I) that has a purity by weight (and/or by GC or HPLC) of at least about 95%, or at least about 96%, or at least about 97%, or at least about 98%, wherein the crude compound of Formula (I) has not been purified or has been purified only by fractional distillation. In some embodiments, the method provides the compound of Formula (I) as a crude compound of Formula (I) that is substantially in monomeric form, or that comprises less than about 5% by weight, or less than about 3%, by weight, of dimeric and/or oligomeric compounds, wherein the crude compound of Formula (I) has not been purified or has been purified only by fractional distillation.

In some embodiments is a method of preparing a compound of Formula (I-A):

(I-A)

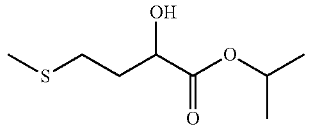

comprising:

(a) treating a compound of Formula (II-A):

(II-A)

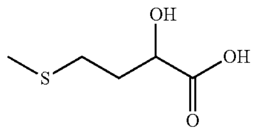

with acetyl chloride to provide a compound of Formula (III-A):

(III-A1)

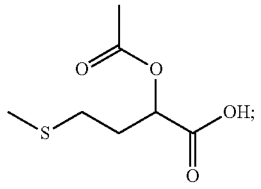

(b) reacting the compound of Formula (III-A1) with isopropanol to provide a compound of Formula (IV-A):

(IV-A)

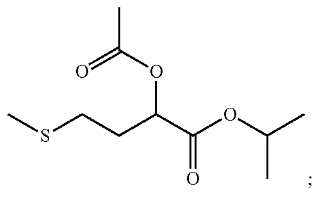

;

and (c) treating the compound of Formula (IV-A) with an aqueous base to provide the compound of Formula (I-A).

In some embodiments is a method of preparing a compound of Formula (I-A):

(I-A)

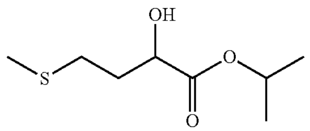

comprising:

(a) combining a compound of Formula (II-A):

(II-A)

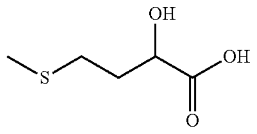

and n-heptane;

(b) drying the compound of Formula (II-A) by azeotropic distillation;

(c) adding n-heptane as a nonpolar solvent to the dried compound of Formula (II-A);

(d) treating the dried compound of Formula (II-A) in heptane with acetyl chloride to provide a compound of Formula (III-A):

(III-A1)

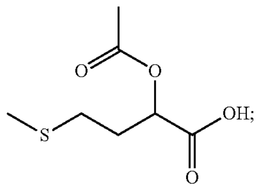

(e) reacting the compound of Formula (III-A1) with isopropanol in a two phase reaction mixture comprising a hydrophilic phase and a hydrophobic phase, to provide a compound of Formula (IV A):

(IV-A)

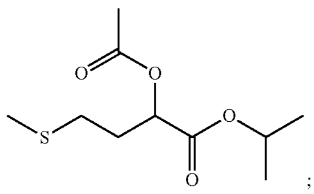

;

(f) treating the compound of Formula (IV-A) with an aqueous base to provide the compound of Formula (I-A) in the hydrophobic phase of the reaction mixture; and (g) separating the hydrophobic phase from the hydrophilic phase base to provide the compound of Formula (I-A).

In some embodiments is a method of preparing a compound of Formula (I-A):

(I-A)

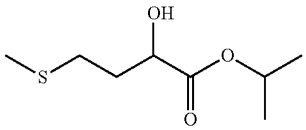

comprising:

(a) treating a compound of Formula (II-A):

(II-A)

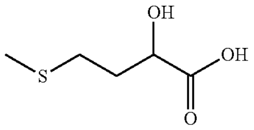

with acetyl chloride to provide a compound of Formula (III-B1):

(III-B1)

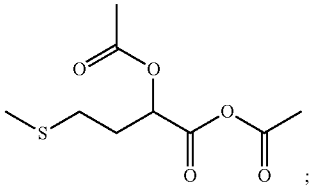

;

(b) reacting the compound of Formula (III-B1) with isopropanol to provide a compound of Formula (IV-A):

(IV-A)

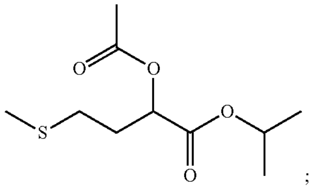

;

and (c) treating the compound of Formula (IV-A) with an aqueous base to provide the compound of Formula (I-A).

In some embodiments is a method of preparing a compound of Formula (I-A):

(I-A)

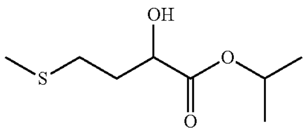

comprising:

(a) combining a compound of Formula (II-A):

(II-A)

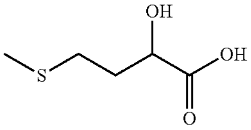

and n-heptane;

(b) drying the compound of Formula (II-A) in n-heptane by azeotropic distillation;

(c) adding n-heptane as a nonpolar solvent to the dried compound of Formula (II-A);

(d) treating the dried compound of Formula (II-A) in n-heptane with acetyl chloride to provide a compound of Formula (III-B1):

(III-B1)

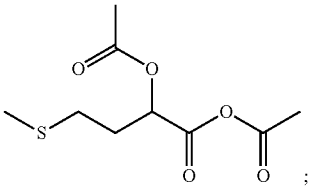

;

(e) reacting the compound of Formula (III-B1) with isopropanol in a two phase reaction mixture comprising a hydrophilic phase and a hydrophobic phase, to provide a compound of Formula (IV-A):

(IV-A)

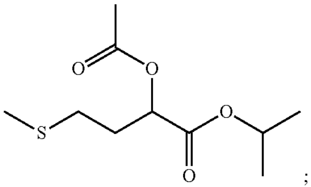

;

(f) treating the compound of Formula (IV-A) with an aqueous base to provide the compound of Formula (I-A) in the hydrophobic phase of the reaction mixture; and (g) separating the hydrophobic phase from the hydrophilic phase base to provide the compound of Formula (I-A).

In some embodiments, the method provides a reaction mixture comprising the compound of Formula (I) or Formula (I-A), and the method further comprises concentrating the reaction mixture to provide a crude residue. In some embodiments, the method further comprises adding base to the reaction mixture or the crude residue, optionally where the base is sodium acetate, aqueous NaOH, such as 0.1 to 10 N aqueous NaOH, or 5 N NaOH, aqueous $NaHCO_3$, aqueous $K_2CO_3$, or aqueous $Na_3PO_4$, preferably where the base is 0.1 to 10 N aqueous NaOH, or 5 N NaOH, to increase the pH to a range of from about 5 to about 10, or about 5 to about 9, or about 5 to about 8 to provide a basic mixture, and extracting the compound of Formula (I) or Formula (I-A) from the basic mixture into at least one nonpolar solvent to provide an extract. In some embodiments, the at least one nonpolar solvent is chosen from petroleum ether, toluene, methyl tert-butyl ether, hexane, cyclohexane, hexanes, n-heptane, octane, nonane, decane and benzene. In some embodiments, the at least one nonpolar solvent is chosen from hexane, hexanes, n-heptane, octane, nonane, and decane. In some embodiments, the at least one nonpolar solvent is n-heptane. In some embodiments, the volume of n-heptane is about 1 to 10 mL, or about 1 to 5 mL, or about 1 to 3 mL, or about 2 mL per kilogram of the calculated HMBi yield or the mass of the crude residue (e.g., the calculated or estimated amount of HMBi present in the mixture). In some embodiments, the extracting is done with n-heptane that is at a temperature of from about 25° C. to 50° C., or from about 30° C. to about 50° C., from about 30° C. to about 40° C., before the extracting. In some embodiments, the extract comprises the compound of Formula (I) or Formula (I-A) in at least about 95% purity by GC, by HPLC, or by weight. In some embodiments, the method comprises removing the at least one nonpolar solvent from the extract, optionally by distillation, to provide the compound of Formula (I) or Formula (I-A) in at least about 95% purity by GC, by HPLC, or by weight.

In some embodiments, the reacting provides a reaction mixture comprising the compound of Formula (I) or Formula (I-A), and the method further comprises adding base to the reaction mixture, optionally where the base is solid sodium acetate, to increase the pH to a range of from about 5 to about 10, or about 5 to about 9, or about 5 to about 8 to provide a basic mixture, drying the basic mixture using a drying agent to provide a dried basic mixture, and purifying the compound of Formula (I) or Formula (I-A) from the dried basic mixture by distillation to provide the compound of Formula (I) or Formula (I-A) in at least about 95% purity by GC, by HPLC, or by weight.

Compound Products

In some embodiments, the reacting provides a crude compound of Formula (I) or Formula (I-A) that has a purity by weight (and/or by GC or HPLC) of at least about 80%, or at least about 90%, or at least about 95%, or at least about 96%, or at least about 97%, or at least about 98%, wherein the crude compound of Formula (I) or Formula (I-A) has not been purified or has been purified only by fractional distillation. In some embodiments, the reacting provides a crude compound of Formula (I) or Formula (I-A) that is substantially in monomeric form, or that comprises less than 5% by weight, or less than 3%, by weight, of dimeric and/or oligomeric compounds, wherein the crude compound of Formula (I) or Formula (I-A) has not been purified or has been purified only by fractional distillation.

In some embodiments, the disclosure relates to a compound of Formula (I) or Formula (I-A) prepared as in a method described herein. In some embodiments, the disclosure relates to a compound of Formula (I) or Formula (I-A), wherein the compound has a purity by weight (and/or by GC or HPLC) of at least about 80%, or at least about 90%, or at least about 95%, or at least about 96%, or at least about 97%, or at least about 98%, and the compound has not been purified or has been purified only by fractional distillation. In some embodiments, the compound is substantially in monomeric form, or is mixed with less than about 5%, or less than about 3%, by weight, of dimeric and/or oligomeric compounds.

In some embodiments, the HMBi (Formula (I-A)) product has one or more of the following specifications: (a) at least about 95% by weight or by HPLC analysis HMBi monomer content and chemical purity; (b) water content of less than about 0.5% by Karl Fischer analysis; (c) pH less than about 6.0 (measured at 1% concentration in water); and (d) a n-heptane content of less than about 5000 ppm by HPLC, or ranging from about 1 to about 4999 ppm, or from about 100 to about 4000 ppm, or about 250 to about 3000 ppm, or about 400 to about 2000 ppm, or about 500 to about 1900 ppm.

Where a compound of Formula (II) or (II-A) is in a starting material mixture with HMBA dimer/oligomer materials (e.g., commercially available 88% HMBA), the esterification reactions described herein can depolymerize the dimer/oligomers and convert the resulting monomers to HMBi. Therefore, the presently described reactions can achieve a higher than 100% yield of HMBi relative to the amount of monomeric Formula (II)/(II-A) in the starting material. In some embodiments, HMBA is the starting material and is used in about 95% purity. In some embodiments, the HMBA starting material is 95% purity and is anhydrous. In some embodiments, the HBMA starting material is of 88% purity, which includes monomer, dimer, and oligomer materials, and water. In some embodiments, the HMBA starting material is not the direct product of hydrolysis of 2-hydroxy-4-(methylthio)butanenitrile (HMBN). In some embodiments, the HMBA starting material is derived from α-hydroxy-γ-butyrolactone or 2-hydroxy-4-(methylthio)butanamide.

Also disclosed herein is compound of Formula (I) or Formula (I-A) prepared by any of the methods described herein. In some embodiments is a compound of Formula (I) or Formula (I-A), wherein the compound has a purity by weight (and/or by GC or HPLC) of at least about 95%, or at least about 96%, or at least about 97%, or at least about 98%, and the compound is a crude compound, has not been purified, and/or has been purified only by fractional distillation. In some embodiments, the compound is the compound of Formula (I), wherein $R^1$ is $—CH_2CH_2—S—CH_3$ and $R^2$ is isopropyl, or the compound is the compound of Formula (I-A). In some embodiments, the compound is substantially in monomeric form, or is mixed with less than about 5%, or less than about 3%, by weight, of dimeric and/or oligomeric compounds.

In another aspect, the present disclosure relates to a composition comprising at least 95% by weight or by HPLC analysis of the compound of Formula (I-A) (HMBi) and from about 1 to 4999 ppm n-heptane as an impurity. In some embodiments, the composition comprises from about 1 to about 1000 ppm n-heptane as an impurity.

Animal Feed Compositions and Uses

In some aspects, the present disclosure relates to an animal feed composition comprising the compound of Formula (I) or Formula (I-A) as described herein. In some embodiments, animal feed composition is suitable for administration to ruminants, such as cattle, cows, sheep, antelope, deer, giraffes, bovines (e.g., bison, buffalo, or yak), goats, and/or gazelles. In some embodiments, the animal feed composition is a cow feed composition, such as a dairy cow feed composition, or an additive for cow feed, such as dairy cow feed. In some embodiments, the animal feed composition is a dairy cow feed composition.

In some embodiments, the animal feed composition is an animal feed or an animal feed additive. In some embodiments, the animal feed additive is in liquid or solid form, wherein the liquid form comprises the compound and optionally a liquid carrier, and the solid form comprises the compound admixed with a solid carrier, optionally wherein the solid carrier is silica (silicon dioxide), optionally wherein the ratio of the compound to solid carrier is from about 5:1 to about 1:5, or is 3:2. In some embodiments, the feed composition is liquid feed additive or a solid feed additive. In some embodiments, the animal feed composition is drinking water additive. In some embodiments, the liquid feed additive or drinking water additive has a pH ranging from about 4.0 to about 7.5.

In some embodiments of the animal feed composition, $R^1$ is —$CH_2CH_2$—S—$CH_3$ and $R^2$ is isopropyl. In some embodiments, the compound is the compound of Formula (I-A).

In some embodiments, the disclosure relates to a method of supplying bioavailable methionine to a dairy cow comprising administering to the cow the compound or animal feed composition described herein. In some embodiments, administering comprises feeding to the cow a feed composition containing the compound. In some embodiments, the disclosure relates to a method of supplying at least about 50% bioavailable methionine to a dairy cow comprising administering to the cow the compound or animal feed composition as described herein. In some embodiments, the disclosure relates to a method of improving milk obtained from a dairy cow, comprising supplying to the cow the compound or animal feed composition as described herein. In some embodiments, the improvement in the milk comprises increased protein content in the milk. In some embodiments, the improvement in the milk comprises increased fat content in the milk. In some embodiments, the disclosure relates to a method of improving the condition of a cow comprising supplying to the cow the compound or animal feed composition as described herein. In some embodiments, the improvement in the condition of the cow comprises improved fertility. In some embodiments, the improvement in the condition of the cow comprises improved liver function. In some embodiments, the improvement in the condition of the cow comprises an increase in energy.

Method of HMBi Isolation/Extraction

Also disclosed herein is a method of extracting or isolating HMBi by partitioning a mixture of HMBi and at least one impurity selected from HMBA, HMBA dimer, HMBA oligomer, HMBi dimer, and HMBi oligomer, between a n-heptane phase and a basic aqueous phase. In some embodiments, the basic aqueous phase is at a pH of from about 5 to about 10, or about 5 to about 9, or about 5 to about 8.

In some embodiments the partitioning of HMBi into the n-heptane phase occurs when n-heptane is added to the reaction mixture after the reaction is complete, or near complete, or is stopped. In some embodiments the partitioning of HMBi into the n-heptane phase occurs when n-heptane is added to the reaction mixture after 12-24 hours, or in 16 to 24 hours, or in 12 to 16 hours, or in 14 to 18 hours.

Also disclosed herein is a method of extracting or isolating HMBi by partitioning a mixture of HMBi and at least one impurity chosen from HMBA, HMBA dimer, HMBA oligomer, HMBi dimer, and HMBi oligomer, between a hydrophobic phase and a hydrophilic phase of a two phase reaction. In some embodiments, the hydrophobic phase comprises n-heptane. In some embodiments, the hydrophilic phase comprises isopropanol. In some embodiments, the HMBi is partitioned in the hydrophobic phase and the at least one impurity is partitioned into the hydrophilic phase during the reaction.

In some embodiments the partitioning of HMBi into the n-heptane phase occurs during the reaction process by adding n-heptane to the reaction mixture along with the HMBA, acetyl chloride, isopropyl alcohol, and/or any other combination of reactants as described herein. In some embodiments partitioning of HMBi into the n-heptane phase occurs when an aqueous base is added to the reaction mixture. In some embodiments adding the aqueous base to the reaction mixture increases the amount of HMBi in the n-heptane phase.

Without wishing to be bound by any particular theory, it is believed that when n-heptane is added to the reaction mixture, creating a two-phase reaction mixture, the more hydrophobic products move across the hydrophobic/hydrophilic phase boundary from the hydrophilic phase (based on the partition and/or distribution coefficients) of the reaction mixture into the hydrophobic phase of the two phase reaction mixture. Based on Le Chatelier's principle, the equilibrium of the reaction can be shifted to favor formation of product, while simultaneously protecting the product from undergoing undesirable side reactions in the hydrophilic phase, by partitioning the product into the hydrophobic phase from the hydrophilic phase.

In some embodiments, the nonpolar solvent is chosen from petroleum ether, toluene, methyl tert-butyl ether, hexane, cyclohexane, hexanes, n-heptane, octane, nonane, decane and benzene. In some embodiments, other nonpolar solvents, for example, petroleum ether, toluene, methyl tert-butyl ether, hexane, cyclohexane, octane, decane and benzene may be used as the hydrophobic phase.

In some embodiments, the volume of n-heptane is about 1 to 10 mL, or about 1 to 5 mL, or about 1 to 3 mL, or about 2 mL per kilogram of the calculated HMBi yield or the mass of the crude residue (e.g., the calculated or estimated amount of HMBi in the mixture). In some embodiments, the extracting is done with n-heptane that is at a temperature of from about 25° C. to 50° C., or from about 30° C. to about 50° C., from about 30° C. to about 40° C., before the extracting.

In some aspects, any of the reactions described herein may be performed using a continuous flow apparatus.

Aspects of the present disclosure can be further understood in light of the following examples, which should not be construed as limiting the scope of the present disclosure in any way.

Those having ordinary skill in the art will understand that many modifications, alternatives, and equivalents are possible. All such modifications, alternatives, and equivalents are intended to be encompassed herein.

EXAMPLES

Equipment. All mmol-scale experiments were carried out using a 100 mL or 250 mL three-neck round-bottom flask with magnetic stirrer bar, dropping funnel, and thermometer. The reaction flask was equipped with a condenser and a thermometer to monitor the reaction temperature. For reactions run at reflux, the reaction mixture was heated using a silicon oil-bath. For experiments at temperatures below room temperature, a salt/ice cooled mixture bath was used. All kg-scale experiments were carried out using a 5 L glass lined reactor or a 5 L jacketed three-neck vessel flask equipped with two condensers and an overhead stirrer. The concentration and/or purification of intermediates and the crude product were carried out using laboratory scale vacuum distillation unit or column chromatography.

For Examples 1-12, HMBA (minimum 95% purity) containing monomeric HMBA (possibly with mixtures of dimers and/or oligomers); or HMBA (88% purity) containing a mixture of monomers, dimers, and/or oligomers, and 12% water, were used as starting materials as indicated.

General Scheme 1: Transesterification.

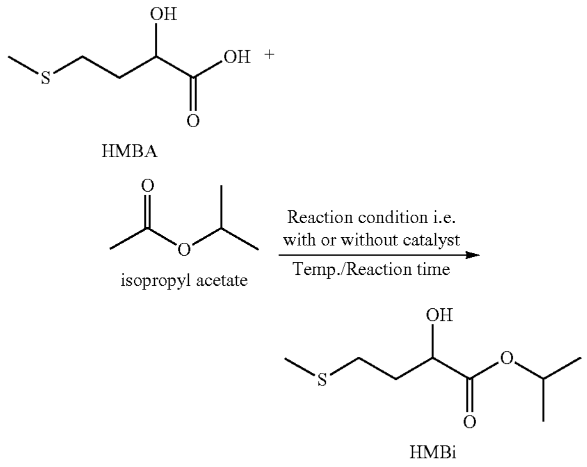

Example 1. Screening Scale Synthesis of HMBi Via Transesterification of HMBA and Various Isopropyl Ester(s)

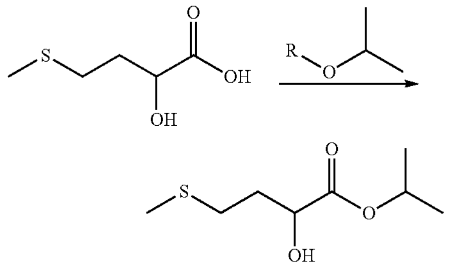

R = HC(O)—, $CH_3C(O)$—, $CH_2$ = CHC(O)—, or $CH_3SO_2$-

HMBA (95.6%; 1.70 g, 1.0 eq) was added into a 100 mL reaction vessel containing 10 eq of isopropyl formate (10 g). No acid catalyst was used in this reaction. The reaction mixture was stirred well and then heated up to 100° C. (or 150° C.) for 7 h. Reactions at elevated temperature were performed in sealed tube. The reaction mixtures before and after reaction were sampled and subjected to HPLC assay. HMBi conversion was monitored by HPLC. Reactions with other isopropyl reagents were performed analogously on a 1 to 2 g scale for 7 h at the noted temperatures. Reactions may also be run at the reflux temperature of the isopropyl reagent.

Table 1 shows the results from screening experiments using six forms of isopropyl esters to react with HMBA under catalyst-free transesterification. The results show that HMBi was generated with isopropyl formate, isopropyl acetate, isopropyl acrylate, and isopropyl methanesulfonate, but not with diisopropyl carbonate or diisopropyl oxalate. For example, HMBi was generated by a reaction between HMBA and isopropyl methanesulfonate at 25° C. for 12 h (with 59% conversion; Entry 15). Reaction of HMBA with other esters at elevated temperature produced HMBi as well (Entries 2, 5, and 11).

TABLE 1

| Entry | Isopropyl Reagent | Reaction temp. (° C.) (RT = room temperature) | % Conversion to HMBi |
|---|---|---|---|
| 1 | 10 eq isopropyl formate | RT | — |
| 2 | 10 eq isopropyl formate | 100 | 29 |
| 3 | 10 eq isopropyl acetate | RT | — |
| 4 | 10 eq isopropyl acetate | 100 | — |
| 5 | 10 eq isopropyl acetate | 150 | 19 |
| 6 | 10 eq diisopropyl carbonate | RT | — |
| 7 | 10 eq diisopropyl carbonate | 100 | — |
| 8 | 10 eq diisopropyl carbonate | 150 | — |
| 9 | 10 eq isopropyl acrylate | RT | — |
| 10 | 10 eq isopropyl acrylate | 100 | — |
| 11 | 10 eq isopropyl acrylate | 150 | 31 |
| 12 | 10 eq diisopropyl oxalate | RT | — |
| 13 | 10 eq diisopropyl oxalate | 100 | — |
| 14 | 10 eq diisopropyl oxalate | 150 | — |
| 15 | 10 eq isopropyl methanesulfonate | RT | 59 |
| 16 | 10 eq isopropyl methanesulfonate | 100 | — |

Example 2. Transesterification of HMBA Via Catalytic Transesterification with Isopropyl Acetate

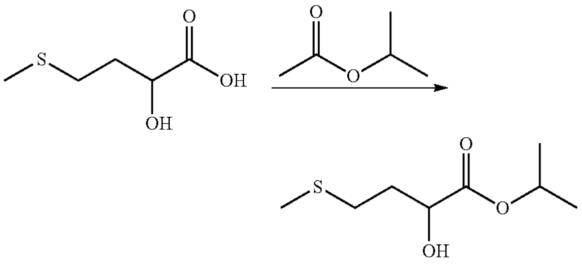

HMBA (95%, 247 g) was diluted in dichloromethane and dried over $MgSO_4$, filtered, and concentrated under vacuum to provide dried HMBA, which was treated with isopropyl acetate (500 mL). The reaction mixture was heated up and the reaction was carried out at reflux (~80° C.) for 12 h. The reaction was repeated for N=3 (N=number of experiments). The reaction conversion was monitored by gas chromatography to observe the conversion to HMBi during the reaction period. After the reaction was completed, the reaction mixture was cooled to room temperature and was partitioned between 250 mL ethyl acetate and 250 mL water (2×). The collected organic phase was further washed with 300 mL saturated $NaHCO_3$ (2×) and with 300 mL of saturated NaCl solution. The organic layer was dried over $Na_2SO_4$, filtered, and concentrated under reduced pressure to obtain crude HMBi (210 g, 75%). The crude was purified by distillation to determine the isolated yield. The product purity was determined by gas chromatography and by $^1H$ NMR.

In some experiments, the HMBi product (50% yield) was isolated after column chromatography. In other experiments, the reaction is performed for a time from 4 to 12 h.

Example 3. Transesterification of HMBA Via Transesterification with Isopropyl Acetate on Kilogram Scale with or without Catalyst

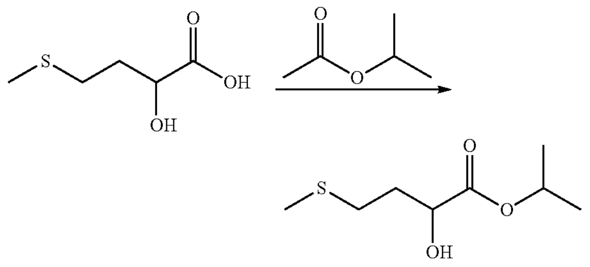

HMBA (88%, 1009.95 g) was diluted with dichloromethane (1.13 L), dried over $MgSO_4$, filtered, and concentrated under vacuum to provide dried HMBA. The dried HMBA was charged into a reaction vessel containing 2 L of isopropyl acetate (2.54 eq.). For the non-catalyst transesterification, the reaction mixture was heated to reflux temperature (~90-95° C.) for 18 h. For the catalytic transesterification, 5% wt. (57.35 mL) HCl (conc. 36%) or 5% wt. $H_2SO_4$ (98%) was added and thereafter the reaction mixture was heated to reflux with stirring. The reaction conversion in each case was monitored via HPLC (off-line measurement). HPLC analyses during the non-catalyst reaction, HCl reaction, and $H_2SO_4$ reaction detected no production of isopropyl alcohol (See FIGS. 1A and 1B). HPLC analysis was conducted as follows:

Eluent: 650 mL of milliQ water+2 mL of 85% phosphoric acid+350 mL of acetonitrile Column: OOG-4633-EO, Kinetex 5 μm EVO C18, 100 Å, size: LC-column: 250×4.6 mm Detector: Spectrosystem UV2000 at 210 nm; Flow-rate: 1 mL/min. Oven temp: 30° C.

When the reaction was complete, the reaction mixture was cooled to below 50° C. and the isopropyl acetate (~700 mL) was distilled off under reduced pressure. The residue was treated with 100 g of sodium acetate or a saturated $NaHCO_3$ solution (250 mL) to adjust the pH value ~8 to 10. The mixture was diluted with pre-warmed n-heptane (1500 mL) and the resulting mixture was stirred for 60 minutes (to extract HMBi). The organic phase was separated and the aqueous layer was extracted with another 500 mL of pre-warmed n-heptane. The organic phases were combined and further washed with 500 mL water (3×) and 1000 mL of satd. NaCl solution. The organic layer was concentrated under vacuum to obtain crude HMBi. The crude material was then treated with 5% wt. (relative to crude mass) of activated carbon at 50° C. for 2 h to obtain a decolorized crude material. The mixture was filtered, and the filtrate was distilled to remove n-heptane and then was concentrated under vacuum. The product yield and purity were determined by HPLC, and showed a crude purity of 78% before the work-up using n-heptane extractions.

The product was obtained as pale to light-yellow oil with a product purity of ≥95% monomeric ester and by which the structure of the product was confirmed by $^1H$-NMR. $^1H$ NMR (400 MHz, $CDCl_3$) δ5.08 (hept, J=6.3 Hz, 1H), 4.24 (dd, J=7.9, 3.8 Hz, 1H), 2.97 (br, 1H), 2.67-2.55 (m, 2H), 2.10-2.01 (m, 4H), 1.93-1.84 (m, 1H), 1.27 (d, J=1.9 Hz, 3H), 1.26 (d, J=2.2 Hz, 3H).

Reactions with isopropyl acetate and acid catalyst or with isopropyl methanesulfonate were performed analogously to the procedure described above. Results for the experiments are shown in Table 2.

TABLE 2

Kilogram scale synthesis of HMBi

| Entry | Reaction Starting Material (Purity) and Reagent(s) | Reaction Temp and Time | Yield (%) HMBi Purity (%) |
|---|---|---|---|
| 1 | HMBA (88%) and isopropyl acetate | 95° C./18 h | Yield: 29.8% Purity: 96% |
| 2 | HMBA (88%) and isopropyl acetate in presence of 5% $H_2SO_4$ | 95° C./15 h | Yield: 48% Purity: 95% |
| 3 | HMBA (88%) and isopropyl acetate in presence of 5% of conc. HCl | 95° C./10 h | Yield: 71% Purity: 98.8% |
| 4 | HMBA[1] (88%) and isopropyl methanesulfonate | 80° C./16 h | Yield: 17% Purity: 95% |

[1]HMBA 500 g was used as starting material.

HPLC results shown in FIGS. 1A, 1B, 2A, 2B, 3A and 3B are summarized in the tables below.

TABLE 2A

Figure 1B:
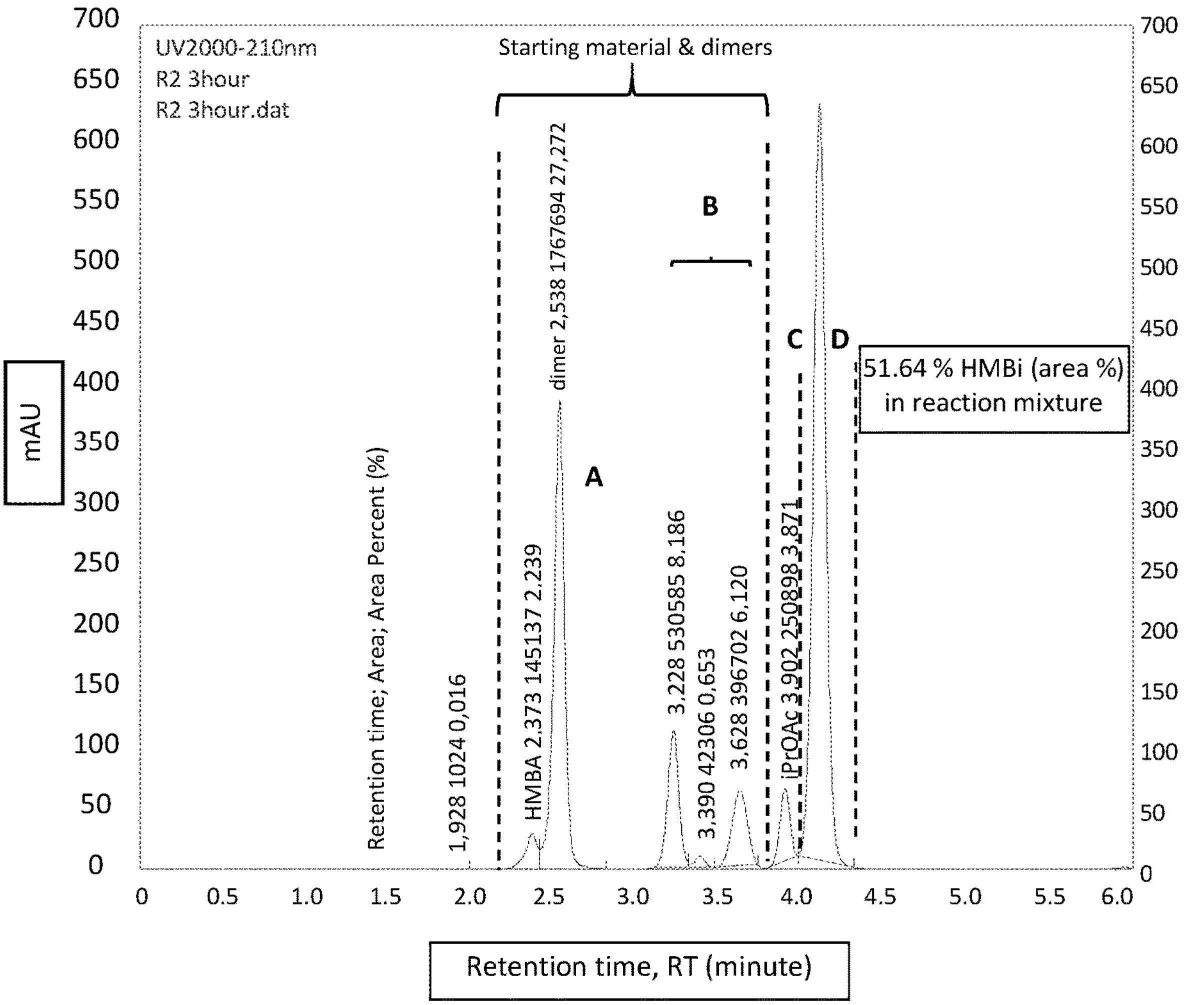
FIG. 1B is an HPLC chromatogram depicting results for HPLC analysis of the reaction mixture during the reaction of HMBA and isopropyl acetate, in the presence of 5% aq. HCl, as described in Example 3.

Summary of HPLC Analysis shown FIG. 1A

| Peak | Retention time (RT) min/ Area (Area percent) | Obtained product (measured by HPLC) |
|---|---|---|
| A | 2.34 min/ 63953 (0.482%) 2.54 min/ 39431 (0.297%) | Starting material HMBA & dimers |
| B | 2.94 min/ 88737 (0.668%) 3.23 min to 3.52 min/28116 (0.212%) | Starting material dimer |
| C | 4.098 min/Area: 13028731 (98.125%) | HMBi |

TABLE 2B

Summary of HPLC Analysis shown FIG. IB

| Peak | Retention time (RT) min/ Area (Area percent) | Obtained product (measured by HPLC) |
|---|---|---|
| A | 2.37-2.53 min/ 1912831 (29.5%) | Starting material HMBA (monomer & dimers) |
| B | 3.22 min-3.62 min/ 969593 (14.95%) | Starting material HMBA dimers |
| C | 3.902 min/250898 (3.87%) | iPrOAc (as reaction solvent & transesterification agent |
| D | 4.11 min 3347272 (51.64%) | HMBi in reaction mixture after 4 h of reaction time |

TABLE 2C

Figure 2A:
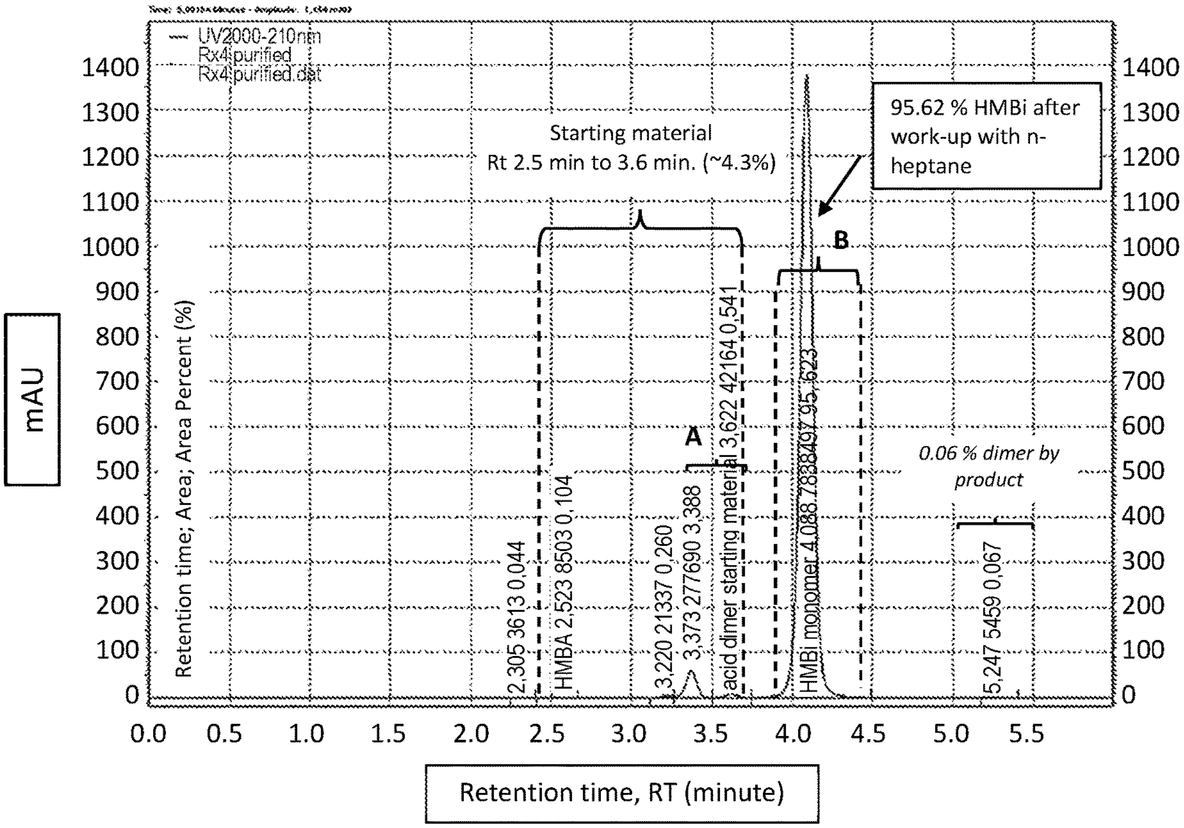
FIG. 2A is an HPLC chromatogram depicting the results of a non-catalytic transesterification reaction of 1.0 eq HMBA (1001.5 g) and 2.54 eq. of iPrOAc (2000 mL) at 90 to 95 C for 18 hours using no added catalyst, as described in Example 3.

Summary of HPLC Analysis shown FIG. 2A

| Peak | Retention time (RT) min/ Area (Area percent) | Obtained product (measured by HPLC) |
|---|---|---|
| A | 3.37 min and 3.62 min/ 277070 (3.39%) 42164 (0.514%) (respectively) | Starting material HMBA & dimers |
| B | 4.088 min/ 7838497 (95.62%) | HMBi peak After work up |

TABLE 2D

Figure 2B:
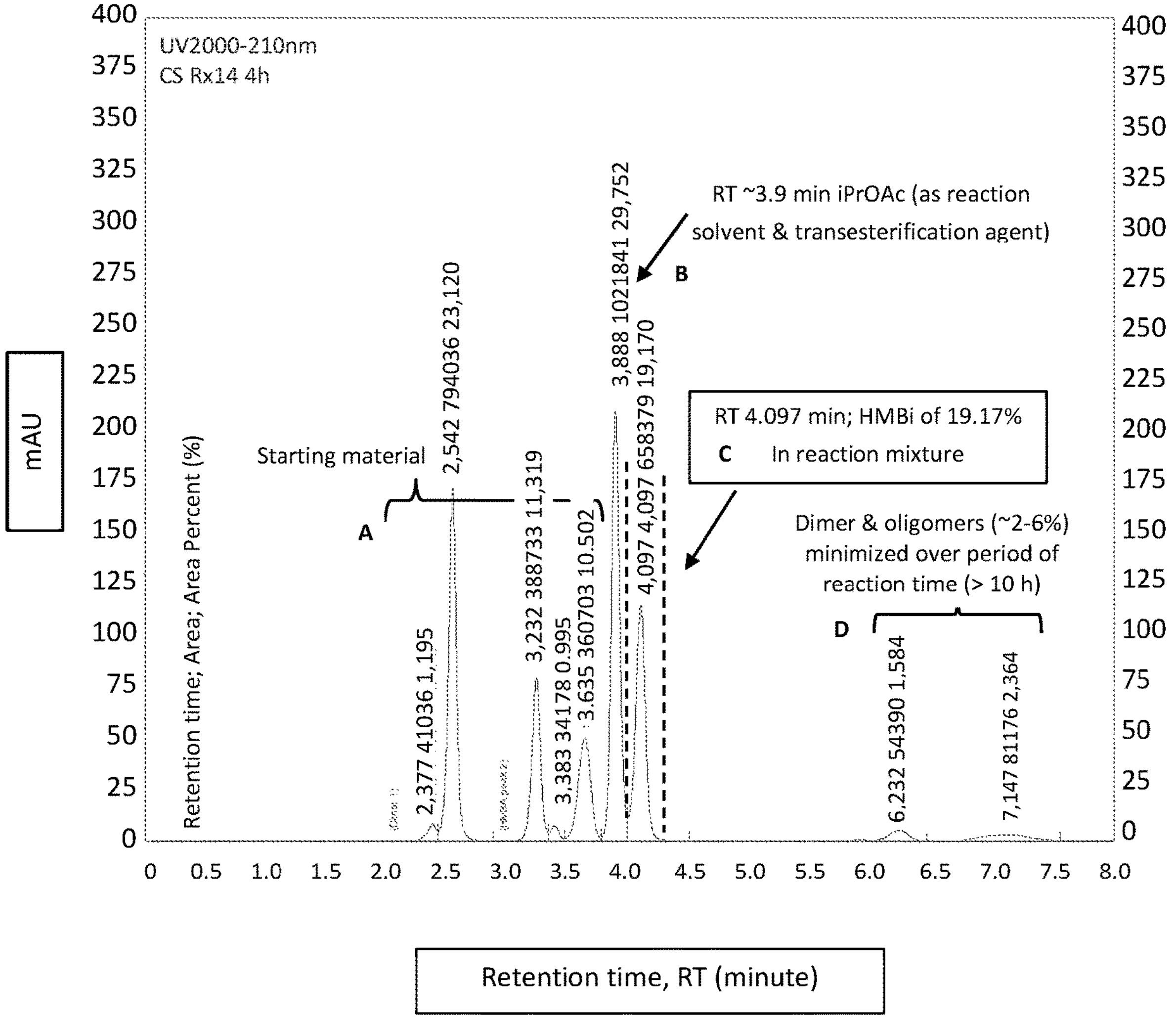
FIG. 2B is an HPLC chromatogram depicting results for HPLC analysis of the reaction mixture during the reaction of 1.0 eq HMBA (1001.5 g) and 2.54 eq. of iPrOAc (2000 mL) at 90 to 95 C for 2 to 18 hours, using no added catalyst, as described in Example 3.

| Summary of HPLC Analysis shown FIG. 2B | | |
|---|---|---|
| Peak | Retention time (RT) min/ Area (Area percent) | Obtained product (measured by HPLC) |
| A | 2.3-3.63 min/1618686 (47%) | Starting materials HMBA & dimers |
| B | 3.888 min/1021841 (29.7%) | iPrOAc (as reaction solvent & transesterification agent |
| C | 4.097 min 658379 (19.17%) | HMBi In reaction mixture |
| D | 6.2 min to 7.5 min/135566 (~2-6%) | Dimer & oligomers minimized over period of reaction time (>10 h) |

TABLE 2E

Figure 3A:
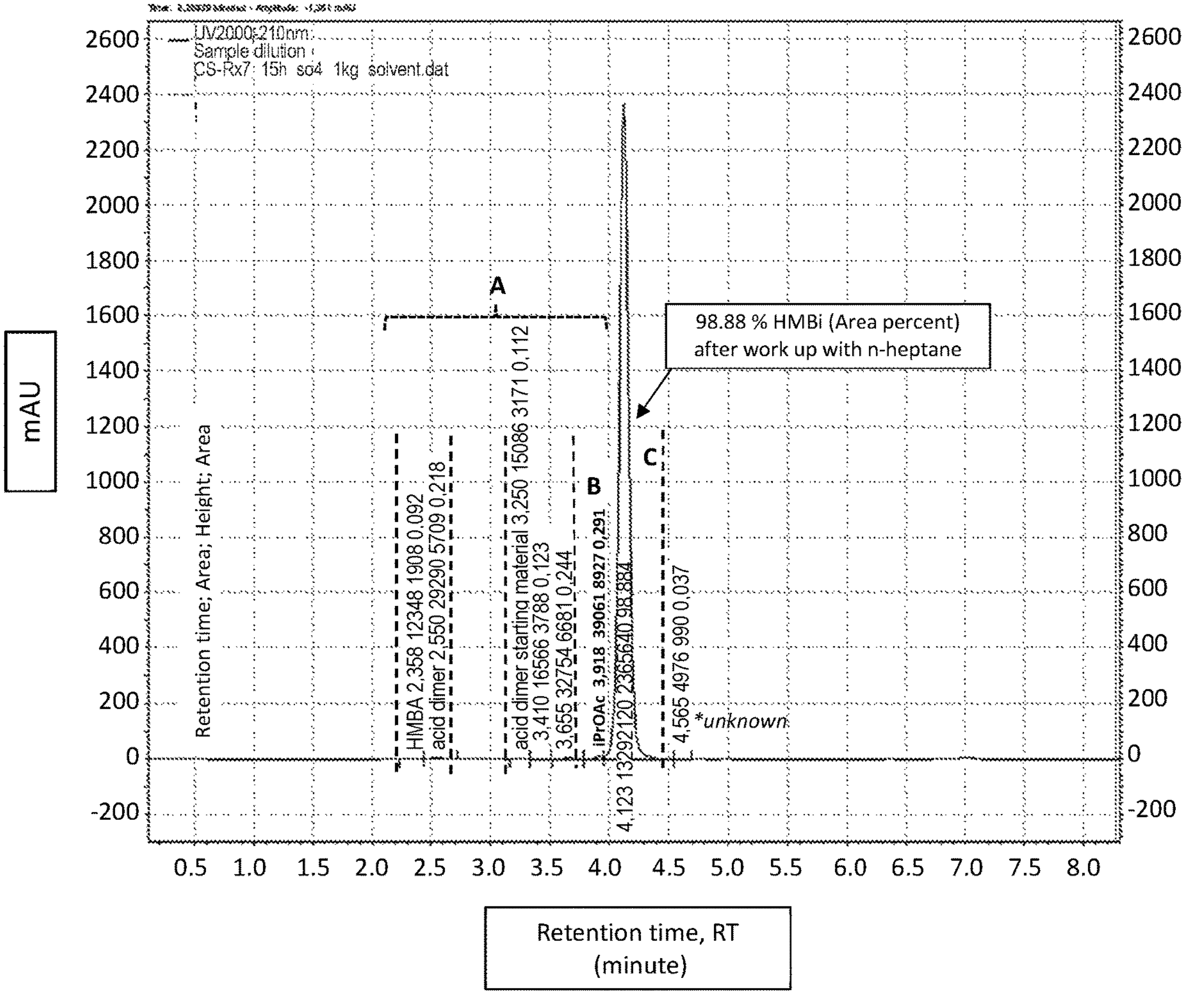
FIG. 3A is an HPLC chromatogram depicting the results of the reaction of 1.0 eq HMBA (1010 g) and 2.54 eq. of iPrOAc (2000 mL), in the presence of 5% aq. $H_2SO_4$, at 90 to 95 C for 18 hours, as described in Example 3.

| Summary of HPLC Analysis shown FIG. 3A | | |
|---|---|---|
| Peak | Retention time (RT) min/ Area (Area percent) | Obtained product (measured by HPLC) |
| A | 2.3-2.55 min (HMBA & dimer) and the region at 3.25-3.65 min/106044 (0.79%) | Starting material |
| B | 3.9 min/ 39061 (0.291%) | Isopropyl acetate; iPrOAc |
| C | 4.12 min/ 2365640 (98.884%) | HMBi |

TABLE 2F

Figure 3B:
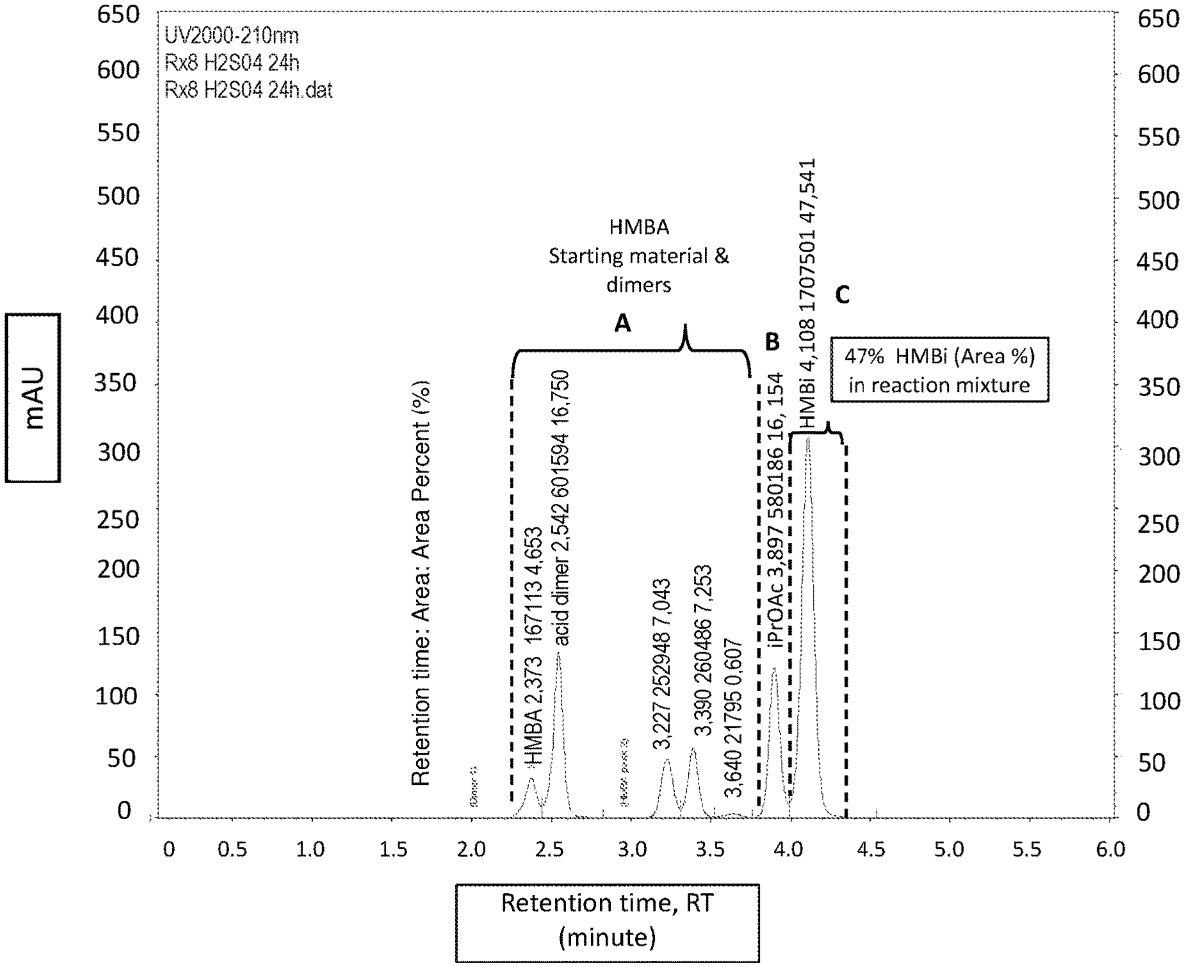
FIG. 3B is an HPLC chromatogram depicting results for HPLC analysis of the reaction mixture during the reaction of 1.0 eq HMBA (1010 g) and 2.54 eq. of iPrOAc (2000 mL), in the presence of 5% aq. $H_2SO_4$, at 90 to 95 C for 18 hours, as described in Example 3.

| Summary of HPLC Analysis shown FIG. 3B | | |
|---|---|---|
| Peak | Retention time (RT) min/ Area (Area percent) | Obtained product (measured by HPLC) |
| A | 2.3-2.54 min (starting material monomer & dimer)/768707 (21%) and at 3.2-3.6 min (dimer) & trace of oligomer/535229 (14.9%) | Starting material HMBA & dimers and/or unknown |
| B | 3.9 min/580186 (16.2%) | Isopropyl acetate; iPrOAc (reaction solvent & reagent) |
| C | 4.1 min/1707501 (47.54%) | HMBi in a reaction mixture |

Example 4. Transesterification of HMBA Via Transesterification with Isopropyl Acetate at 500 kg Scale with Catalyst

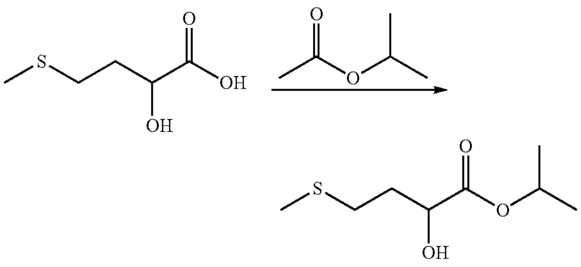

Figure 4:
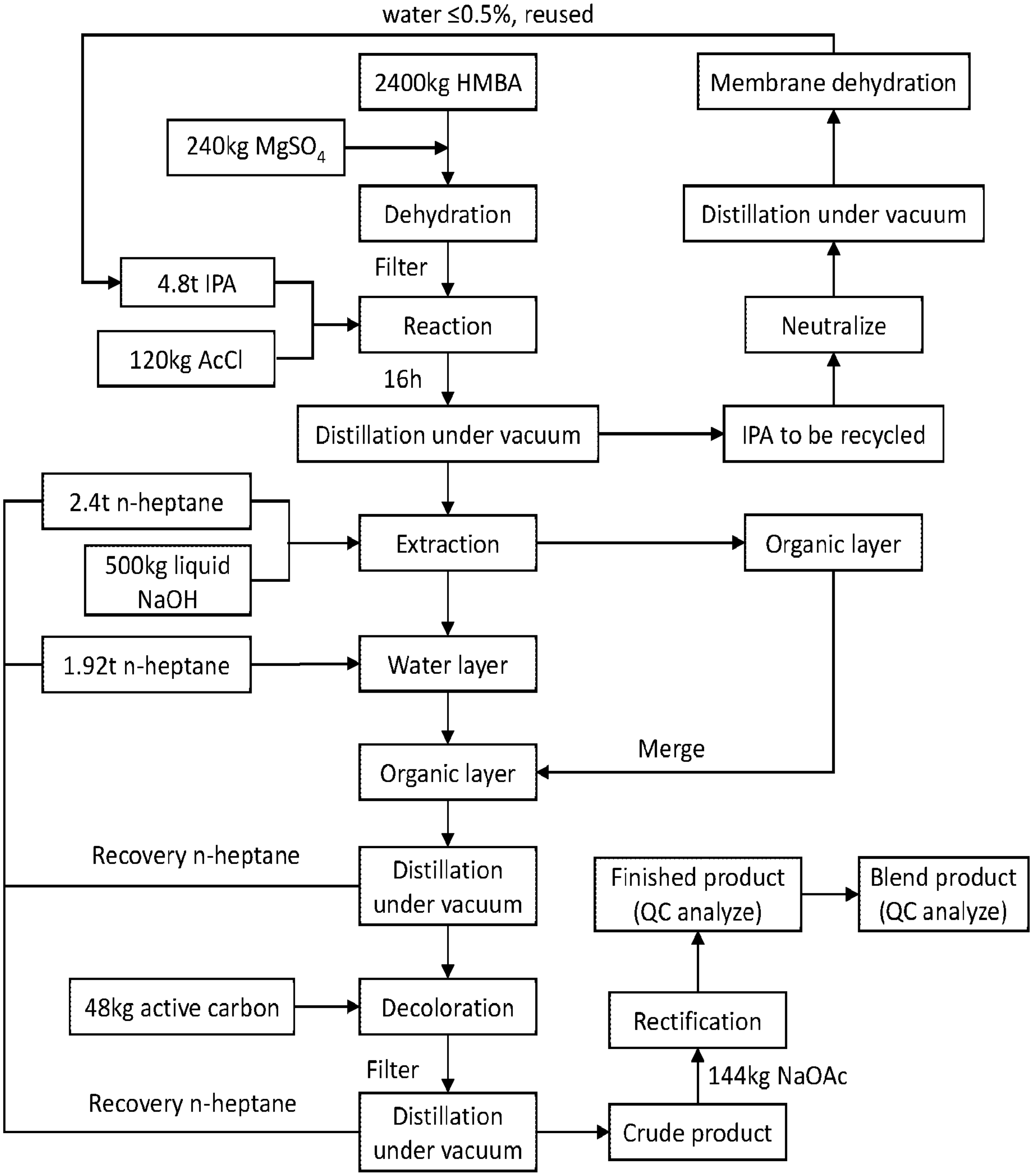
FIG. 4 is an example process flowchart for the synthesis of HMBi according to Example 4 disclosed herein.

HMBA (88%, 500 kg) was charged into a 3000 L stainless steel reactor containing 1000 kg isopropyl acetate. 14.5 kg $H_2SO_4$ (98%) was added in as catalyst. And then the reaction mixture was heated up to 80-90° C. and refluxed for 6 h. The reaction was repeated for N=3 (N=number of experiments). When the reaction was completed, the reaction mixture was cooled to below 50° C., followed by the addition of NaOH solution (20 wt %, 560 kg) to adjust pH to 6.5-7.5. The organic layer and aqueous layer were clearly separated afterwards. The organic phase was then washed with a small amount of water (100 kg) to remove the salt. Subsequently, 40 kg of NaOH solution (20 wt %) were added into the organic phase to adjust pH to 6.5-7.5, which was then concentrated in the 3000 L stainless steel reactor to give crude HMBi product. The product yield and purity were determined by HPLC (57.5% yield, 95% purity). FIG. 4 is an example process flowchart for the synthesis of HMBi.

Example 5. Synthesis of HMBi Through Reaction of HMBA with In Situ-Generated Isopropyl Acetate

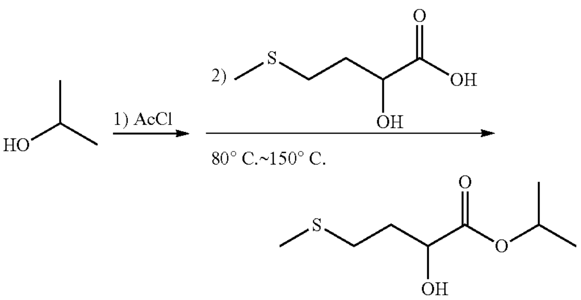

Procedure A: To a stirring sample of isopropyl alcohol (2000 g) was added acetyl chloride (110 mol % relative to HMBA) and the mixture was stirred for 30 min at room temperature. The mixture was treated with HMBA (1000 g) and the resulting mixture was heated at 80 to 90° C. for 2 h. The reaction progress was monitored by gas chromatography. Reaction results were HMBA (0.4% remaining) and HMBi (93.0% GC purity) by gas chromatography (GC).

Procedure B: Additional reactions were performed similarly, for 4 h (0% HMBA remaining; 95.8% HMBi), 6 h (0.5% HMBA remaining; 95.4% GC purity), 8 h (0.3% HMBA remaining; 95.7% GC purity), 10 h (0% HMBA remaining; 97.0% GC purity), 24 h (0% HMBA remaining; 97.0% GC purity), or 48 hours (0% HMBA remaining; 96.4% GC purity) at 80 to 90° C. with 110 mol % acetyl chloride, or for 48 h at 150 to 160° C. with 110 mol % acetyl chloride (73% GC purity), or for 5 h at 50 to 60° C. with 105 mol % (91% GC purity) or 110 mol % (95% GC purity) acetyl chloride. Reaction at 50 to 60° C. with 101 mol % acetyl chloride ran more slowly.

Work-up Procedures: Reactions were with 105 mol % acetyl chloride at 50 to 60° C. for 16 h and were worked up by:

(a) Dilution with ethyl acetate and washing with water until the organic phase was at neutral pH (81% GC purity of reaction mixture);

(b) Concentration under reduced pressure at 50 to 60° C. for 2 h (81% HMBi in a reaction mixture before workup; 89% GC purity after workup);

(c) Concentration under reduced pressure and then stirring the residue at 50 to 60° C. for 8 h (89% GC purity before workup; 86% purity after workup);

(d) Concentration under reduced pressure and then maintaining the residue at room temperature for 3 days (89% GC purity before workup; 83% purity after workup);

(e) Concentration under reduced pressure and then stirring the residue at 120 to 130° C. for 6 h (89% purity before workup; 69% purity after workup);

(f) Neutralization with NaOH solution (to pH 10) and concentration under reduced pressure for 3 h (96% GC purity of HMBi in reaction mixture before workup; 79% purity after workup).

Procedure C: To isopropyl alcohol (160 kg) was added AcCl (5.0 kg) in 10 portions over 10 min (inner temperature below 40 C) with stirring and stirring was continued for 2 h at room temperature. Subsequently, HMBA (100 kg) and isopropyl alcohol (40 kg) were added consecutively. The resulting reaction mixture was heated up to 80 to 90° C. over 1 h and stirred at this temperature for 14 to 16 h. The reaction mixture was monitored by GC. After cooling to 40 to 50° C., isopropyl alcohol (100 L) was recovered by vacuum distillation (−0.07 MPa) for 6 to 8 h. With the temperature maintained at 50 to 65° C., sodium acetate (6.0 kg) was added to adjust the pH value to 5 to 6, and then vacuum distillation was continued until no further isopropyl alcohol was recovered. The obtained HMBi (about 130 kg) was cooled with recirculating water and 40 kg of 5 N NaOH solution was added to adjust the pH value to 8 to 9. The mixture was diluted with n-heptane (140 kg) and stirred for 15 min. The organic layer was separated and the aqueous layer extracted with another 70 kg portion of n-heptane. n-Heptane was removed under vacuum (60 to 70 C, −0.07 MPa) and crude HMBi was obtained as a pale yellow oil in 70 to 75% yield.

The obtained HMBi may be purified by optional treatment with activated carbon to decolorize, followed by distillation to obtain HMBi in at least 95% purity.

Example 6. Pilot Scale Reaction of Anhydrous HMBA with Isopropyl Acetate

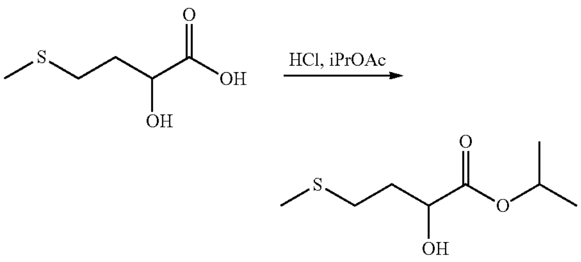

To neat HMBA (88%, 100 kg) was added anhydrous $Na_2SO_4$ (10 kg) or $MgSO_4$ (10 kg), and the resulting mixture was stirred for 2 to 3 hours to remove the majority of water from the HMBA. The mixture was filtered, optionally washing with isopropyl alcohol or isopropyl acetate. To the filtrate was added acetyl chloride (9.14 kg, 0.2 eq.) in 10 portions over 10 minutes, keeping the temperature of the reaction mixture below 40° C., to react with residual moisture and generate HCl in situ. The appropriate amount of acetyl chloride was determined by Karl-Fischer analysis following the $Na_2SO_4$ drying step. The resulting mixture was stirred for 2 h at room temperature. Karl-Fischer analysis was used to confirm no detectable water remained. (On laboratory scale, the drying process can be accomplished by diluting with dichoromethane, drying over $MgSO_4$ or $Na_2SO_4$, filtering, and either concentrating the residue with acetyl chloride to remove remaining water, or treating the filtrate with acetyl chloride to remove remaining water, then concentrating under reduced pressure to remove dichloromethane.) Isopropyl acetate (200 kg) was then added to the reactor. The resulting reaction mixture was heated up to 80 to 90° C. over a period of 1 h and stirred at this temperature for 14 to 16 h. The conversion to HMBi was monitored by GC or HPLC. The reaction mixture was cooled to about 50° C. and isopropyl acetate was recovered by vacuum distillation (−0.07 MPa) for 6 to 10 h (or until no isopropyl acetate remained). The obtained HMBi was then cooled with recirculating water.

Work-up 1: To the cooled HMBi was added 5 N NaOH to adjust the pH value to 8 to 9. To the mixture was added n-heptane (140 kg) and the mixture was stirred vigorously for 15 to 30 min. The organic phase was separated, and the aqueous layer was extracted with another 70 kg of n-heptane. The n-heptane was removed from the combined organic layers at 60 to 70° C. and −0.07 MPa to provide crude HMBi in at least 95% purity. (If the material is brown in color, activated charcoal (2 to 5 kg) can be added directly to the crude HMBi.) The mixture was stirred for 2 to 3 h and filtered, without rinsing, to give a light-colored product.

Work-up 2: To the cooled HMBi (from one or multiple batches) was added sodium acetate to adjust the pH to 5 to 7. The mixture was then dried over $Na_2SO_4$ or $MgSO_4$ and filtered (without rinsing) to remove most moisture. The resulting crude material was purified by fractional distillation to provide purified HMBi in at least 95% purity.

Example 7. Pilot Scale Synthesis of HMBi with In Situ-Generated HCl and in Situ-Generated Isopropyl Acetate

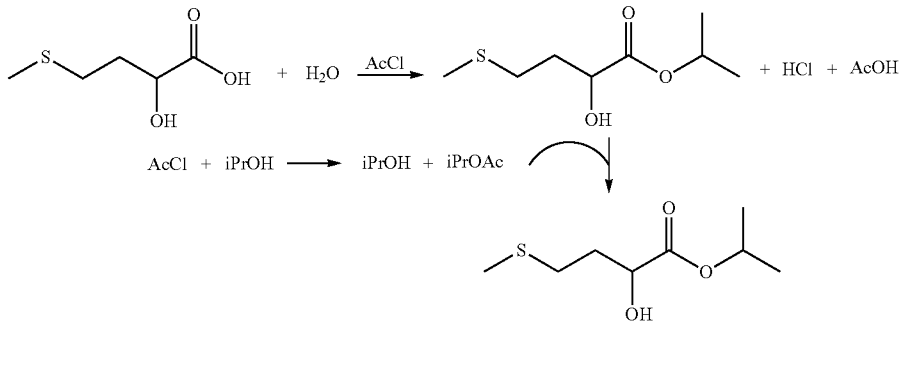

To HMBA (88%, 100 kg) was added anhydrous $MgSO_4$ (10 kg), and the resulting mixture was stirred for 2 to 3 hours to remove the majority of water from the HMBA. The mixture was filtered, rinsing with isopropyl alcohol. To the filtrate was added acetyl chloride (2.6 kg, 0.05 eq.) in 5 portions over 10 minutes, keeping the temperature of the reaction mixture below 40° C., to react with residual moisture and generate HCl in situ to form a dried HMBA/HCl mixture. Karl-Fischer analysis was used to confirm no residual water.

Acetyl chloride (55 kg; 1.05 eq. relative to HMBA) was added to stirring isopropyl alcohol (160 kg) in 20 portions, maintaining the inner temperature below 40° C. The reaction mixture was stirred for 2 h at room temperature to generate isopropyl acetate. To this mixture was added the dried HMBA/HClmixture (assume 100 kg) followed by 30 kg of isopropyl alcohol. The resulting reaction mixture was heated up to 80 to 90° C. over a period of 1 h and stirred at this temperature for 14 to 16 h. The conversion to HMBi was monitored by GC or HPLC. The reaction mixture was cooled to about 50° C. and isopropyl alcohol was recovered by vacuum distillation (−0.07 MPa) for 6 to 10 h (or until no isopropyl alcohol remained), followed by fractional distillation to separate residual isopropyl alcohol and isopropyl acetate. The obtained HMBi was then cooled with recirculating water. The cooled HMBi was subjected to Work-up 1 or 2 as in Example 6 to provide HMBi in at least 95% purity.

Example 8. Pilot Scale Synthesis of HMBi with In Situ-Generated HCl

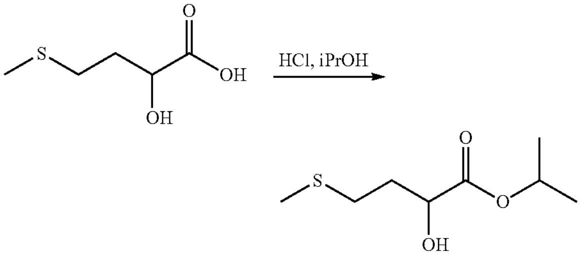

To HMBA (88%, 100 kg) was added anhydrous $Na_2SO_4$ (10 kg), and the resulting mixture was stirred for 2 to 3 hours to remove the majority of water from the HMBA. The mixture was filtered, optionally washing with isopropyl alcohol or isopropyl acetate. To the filtrate was added acetyl chloride (4.57 kg, 0.1 eq.) in 10 portions over 10 minutes, keeping the temperature of the reaction mixture below 40° C., to react with residual moisture and generate HCl in situ. The resulting mixture was stirred for 2 h at room temperature. Subsequently, isopropyl alcohol (200 kg) was added to the reactor. The resulting mixture was heated to 80 to 90° C. over a period of 1 h and stirred at this temperature for 14 to 16 h. The conversion to HMBi was monitored by GC or HPLC. The reaction mixture is cooled to about 50° C. and isopropyl alcohol was recovered by vacuum distillation (−0.07 MPa) for 6 to 10 h (or until no isopropyl alcohol remains). The obtained HMBi was then cooled with recirculating water. The cooled HMBi was subject to Work-up 1 or Work-up 2 as described in Example 6 to provide HMBi in at least 95% purity.

Example 9. Transesterification of HMBA with Triisopropyl Borate

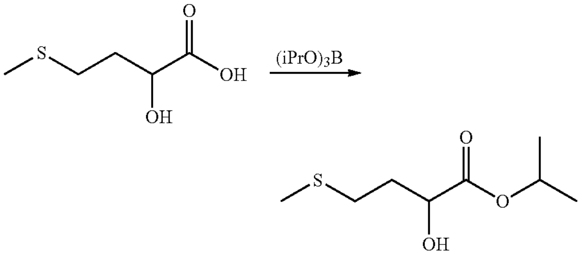

HMBA (88%) was dried as described in the preceding examples. Dried HMBA (250 g, 1 eq.) was treated with triisopropyl borate (626 g, 2 eq.) at 95° C. for 10 h to provide 77% conversion to HMBi. The product was extracted into n-heptane and washed as described above to give HMBi in 72% yield (229.1 g) and 98% purity by HPLC analysis.

General Scheme 2: Esterification Via Stoichiometric Acetylation

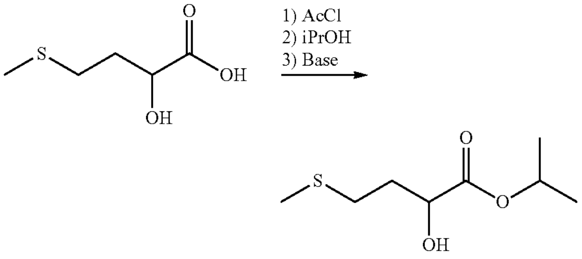

Example 10. Synthesis of HMBi with Stoichiometric Acetyl Chloride and Isopropanol

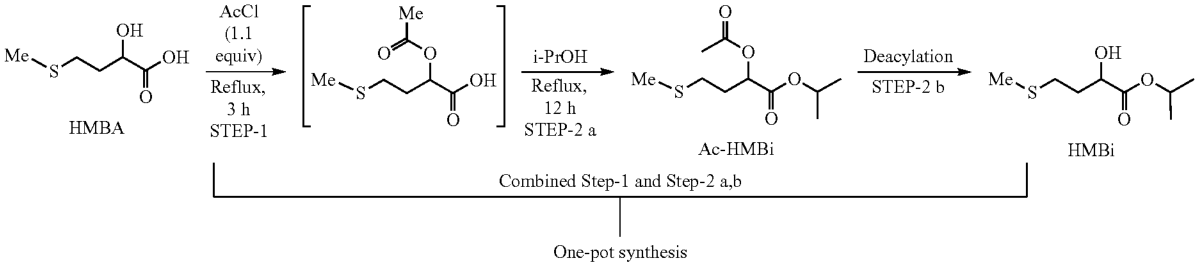

HMBA Ac-HMBi HMBi

Acetyl chloride (10 g, 1.1 eq.) was added dropwise to HMBA (5 g), while maintaining the temperature below room temperature. The reaction was stirred at room temperature for 3 h until 2-acetyoxy-4-(methylthio)butanoic acid (Ac-HMBA) was produced. To the reaction mixture was added isopropyl alcohol (10 g) and the reaction solution was heated to 55° C. for 4 to 12 h, or or 80° C./reflux for 12 h. The mixture was cooled to room temperature and concentrated. The residue was treated with aqueous base (0.1 N NaOH), then extracted with ethyl acetate (50 mL) and washed with water (30 mL), satd. $NaHCO_3$ solution, and satd. NaCl solution, filtered, and concentrated to obtain crude HMBi. The crude was further purified by distillation, and analyzed by gas chromatography and $^1H$ NMR using 4-iodoanisole as an internal standard (95.2% GC purity; 88.1% yield).

Additional experiments were run analogously to the procedure described above, at reaction temperatures of 25, 60, 90, and 120° C., and with 1.0, 1.05, 1.2, and 2.0 equivalents of acetyl chloride. For all of these conditions, HMBi was obtained at least 94% purity and at least 75% crude yield.

TABLE 3

| Entry | Parameter | Reaction Temp/Time | |
|---|---|---|---|
| | | | HMBi Purity (measured by GC) |
| 1 | Step 1: 1.0 equiv HMBA, 1.1 equiv. AcCl | Reflux (~55° C.)/3 h | HMBA conversion to Ac-HMBA |
| | Step 2: Reaction with 1.0 eq. isopropyl alcohol | 80° C. to 90° C./4 h | 95.8% HMBi (GC Purity) in the obtained crude product after work up |
| 2 | Step 1: 1.0 equiv HMBA, 1.05 equiv. AcCl | 25° C./ 4-6 h | HMBA conversion to Ac-HMBA |
| | Step 2: Reaction with 2 eq. isopropyl alcohol | 55° C. to 60° C./16 h | 94.2% HMBi (GC Purity) in a crude product after work up |
| 3 | Step 1: 1.0 equiv HMBA, 1.1 equiv. AcCl | 25° C./4-6 h | HMBA conversion to Ac-HMBA |
| | Step 2: Reaction with 2 eq. of isopropyl alcohol | 80° C. to 90° C./0 h | 97% HMBi (GC Purity) in a crude product after work up |
| | | | HMBi conversion (by GC) |
| 1 | Step 1: 1.0 equiv HMBA, 1.1 equiv. AcCl | Reflux (~55° C.)/3 h | Full conversion to Ac-HMBA with crude yield of 95% |
| | Step 2: Reaction with 1.0 eq. isopropyl alcohol | 80° C. to 90° C./4 h | 95.8% HMBi conversion with crude yield of 86% |
| 2 | Step 1: 1.0 equiv HMBA, 1.05 equiv. AcCl | 25° C./ 4-6 h | Full conversion to Ac-HMBA with crude yield of 93% |
| | Step 2: Reaction with 2 eq. isopropyl alcohol | 55° C. to 60° C./16 h | 94.2% HMBi conversion with crude yield of 84% |
| 3 | Step 1: 1.0 equiv HMBA, 1.1 equiv. AcCl | 25° C./4-6 h | Full conversion to Ac-HMBA with crude yield of 93% |
| | Step 2: Reaction with 2 eq. of isopropyl alcohol | 80° C. to 90° C./10 h | 97% HMBi conversion with crude yield of 91% |

Example 11. Synthesis of HMBi with Stoichiometric Acetyl Chloride and Isopropanol on Kilogram Scale

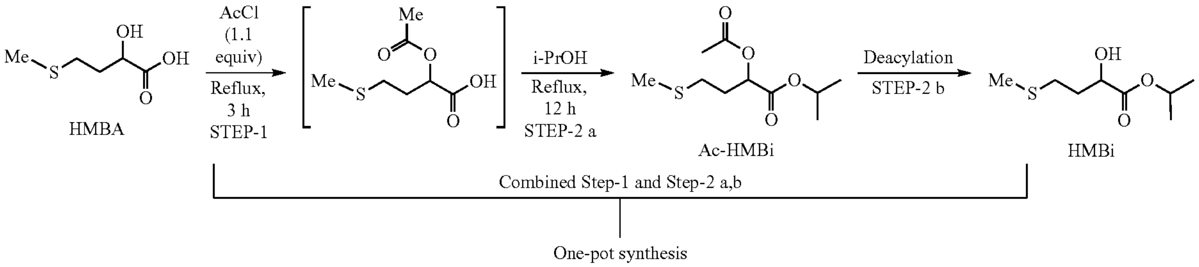

HMBA (95%, 1000 g) was reacted with 1.1 eq. acetyl chloride with stirring at reflux for 3 h. Isopropyl alcohol (2000 mL) was added slowly and the reaction mixture was heated at reflux for 12 h. The mixture was cooled and concentrated. The residue was treated with 0.1 N NaOH (200 mL) and the product was extracted with ethyl acetate (2×400 mL), washed with water (2×1000 mL) and satd. NaCl solution (1000 mL), filtered, and concentrated under vacuum. The crude product was purified by fractional distillation under vacuum to obtain HMBi at least 75% yield.

Example 12A. Synthesis of HMBi with Two Equivalents of Acetyl Chloride and Isopropanol Step 3. After the Step 2 reaction was completed, the reaction mixture was cooled down to room temperature and concentrated. The crude residue was treated with deacylating agent (an aqueous base).

Work-up and Isolation of HMBi Product. The mixture from Step 3 was then diluted with ethyl acetate and washed with 30 mL water. The collected organic phase was further treated by washing twice with the saturated $NaHCO_3$ and brine solution. The organic phase fraction was then filtered and concentrated under reduced pressure to obtain crude HMBi. The crude product was optionally purified by distillation. The purity of crude product was determined by GC and $^1H$ NMR.

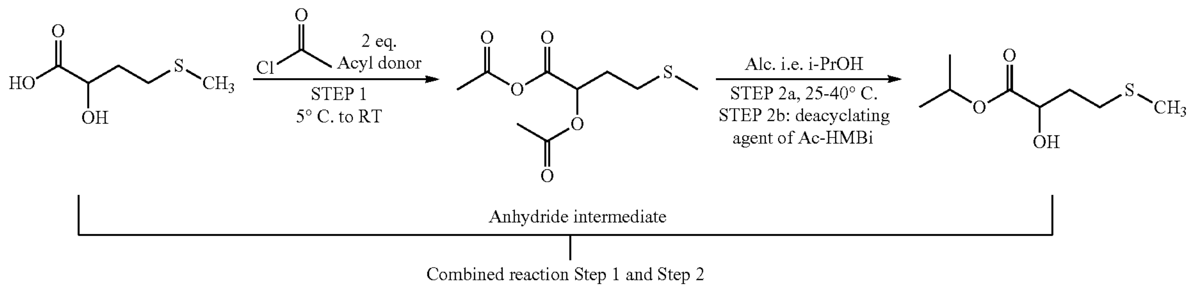

Step 1. Option A. Acetyl chloride (2 equiv.) was added dropwise to HMBA (1 equiv.) neat or in the presence of an organic solvent, while stirring. The reaction temperature was maintained at 10° C. to 15° C. and then slowly raised over a period of time to RT, or until 2-acetoxy-4-(methylthio) butanoic anhydride is formed (as indicated by GC). The reaction was also performed using 2.2 equivalents of acetyl chloride at 55° C. for 3 h to provide a crude yield of at least 93% of Ac-HMBA.

Step 1. Option B. Continuous Flow Acylation. The reaction was performed under a flow chemistry set up (a coiled PFA R&D scale-reactor). A solution of acylation reagent, 2 eq. AcCl in THF, was pumped via a syringe pump to the inlet of T/Y mixer (PTFE) and was combined with and mixed with a flow solution of 1 eq. HMBA (neat or organic solvent). The flow of the reagent was carried out via a dosing pump at a controlled flow rate. The reaction temperature was maintained at RT or, alternatively the mixture is heated until 2-acetoxy-4-(methylthio) butanoic anhydride is formed (as indicated by GC analysis).

Step 2. The obtained intermediate from Step 1 was reacted with 1 eq. isopropyl alcohol solution by stirring the reaction mixture overnight at RT. After addition of alcohol, in this case isopropyl alcohol, the reaction temperature was raised to about 40° C. (or higher) and the condition was maintained until the formation of Ac-HMBi was formed (as indicated by GC analysis). In this case, Steps 1 and 2 were carried out independently. Optionally, the two steps may be carried out within one-pot without isolation of the product of Step 1. The intermediate, the hydroxy-acylated of anhydride (2-Acetoxy-4-(methylthio)butanoic anhydride) is a direct product from Step 1 and is used in Step 2 in the same reaction vessel without isolation.

Step 2 was also carried out using 2 equivalents of isopropyl alcohol to provide a 94% conversion to HMBi and at least 87% crude yield.

Example 12B. Synthesis of HMBi with Two Equivalents of Acetyl Chloride and Isopropanol

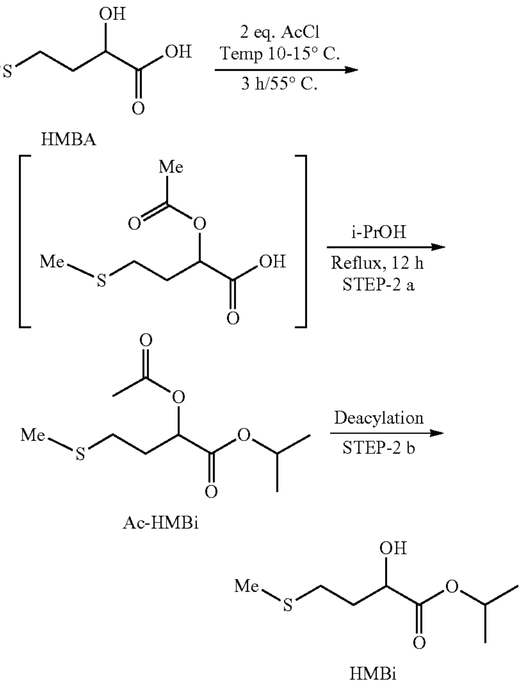

Step 1. Acetyl chloride (2 equiv.) was added dropwise to HMBA (1 equiv.) neat or in the presence of an organic solvent, while stirring. The reaction temperature was maintained at 10° C. to 15° C. and slowly raised over a period of time to RT and reacted at 55° C. for 3 h to provide a crude yield of at least 93% of Ac-HMBA.

Step 2. The obtained intermediate from Step 1 was reacted with 1 eq. isopropyl alcohol solution. After addition of alcohol, in this case isopropyl alcohol, the reaction temperature was raised to about 40° C. (or higher under reflux) and the condition was maintained for 12-15 h until Ac-HMBi was formed (as indicated by GC analysis). In this case, Steps 1 and 2 are carried out independently. Optionally, the two steps may be carried out within one-pot without isolation of the product of Step 1. The intermediate, the 2-acetyoxy-4-(methylthio)butanoic acid (Ac-HMBA) is a direct product from Step 1 and is used in Step 2 in the same reaction vessel without isolation.

Step 3. After the Step 2 reaction was complete, the reaction mixture was cooled down to room temperature and concentrated. The crude residue was treated with deacylating agent (an aqueous base).

Work-up and Isolation of HMBi Product. The mixture from Step 3 was then diluted with ethyl acetate and washed with 30 mL water. The collected organic phase was further treated by washing twice with the saturated $NaHCO_3$ and brine solution. The organic phase fraction was then filtered and concentrated under reduced pressure to obtain crude HMBi. The crude product was optionally purified by distillation. The purity of crude product was determined by GC and $^1H$ NMR.

Step 2 was also carried out using 2 equivalents of isopropyl alcohol to provide a reaction mixture with 80% HMBi purity (GC) after reaction (12-15 h) and 94% HMBi GC purity after work up.

Materials for Examples 13 and 14: HMBA, which contained 88% of HMBA (monomeric, dimeric & oligomer) and 12% water, was pre-dried to a minimum moisture content. Isopropyl alcohol (IPA) (99.8%), n-heptane (AR), AcCl (99%), NaOH (99%), concentrated HCl (37%), sulfuric acid (98%), IPA (99.9%), n-heptane (99.9%), AcCl (99%), NaOH (99%) and sulfuric acid (98%) were used. Lab scale two-phase reactions. Lab scale two-phase reactions were conducted at either 50 g or 100 g scale.

Examples 13-14. One-Pot Synthesis and Extraction of HMBi with Acetyl Chloride (AcCl) and Isopropanol Using a Two-Phase Reaction

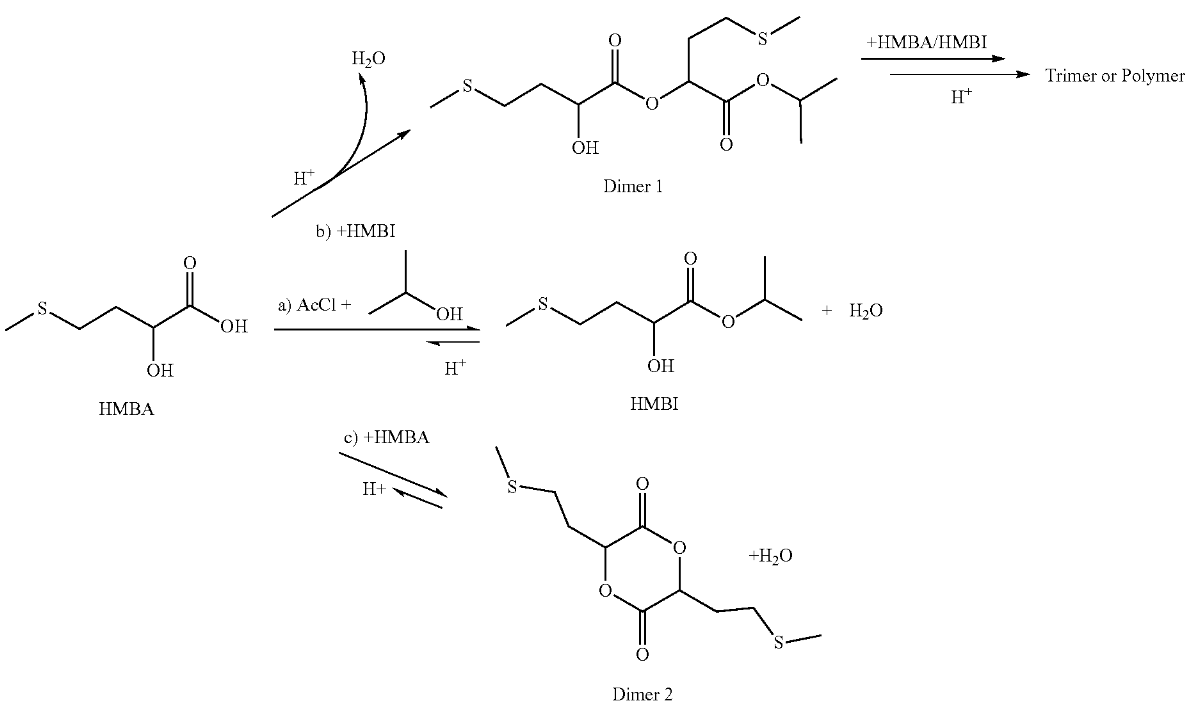

Example 13. One-Pot Synthesis and Extraction of HMBi with Acetyl Chloride (AcCl) and Isopropanol Using a Two-Phase Reaction Drying Step: A drying step was carried out before starting the reaction using azeotrope distillation. HMBA (100 g) was mixed with n-heptane (200 mL) in a 500 mL flask. It was stirred and distilled at 100-110° C. until all the n-heptane was distilled into a collection vessel. The distillation was run for over 3 hours. About 10-11 mL water was visible, settled at the bottom of collection vessel Esterification: To the HMBA or dried HMBA in the flask was then added certain equivalents (eq) of IPA, a certain volume of n-heptane and 0.10 eq of AcCl, as set forth in Table 4. The mixture separated into two phases. The mixture was then heated to 80-90° C. and refluxed for 8-20 hours for esterification. After refluxing, the mixture was cooled to 40-50° C. Sodium hydroxide solution (20% wt/wt) was added dropwise to the mixture to adjust the pH to 8-9, which allowed clear separation of organic layer and aqueous layer. Both layers were sampled for 0.5 mL for the analysis of HMBA and HMBi contents. The conversion rate was calculated by dividing the total HMBi content in each of the organic and aqueous layers by theoretical HMBi output. Some reactions were further processed to work out isolated yield. Briefly, the aqueous layer was back extracted with two portions of n-heptane (0.5 vol each). All organic phases were combined and washed with a small amount of water (10 mL) and then concentrated on a rotary evaporator (Heidolph Hei-VAP Precision ML/G3) to give crude HMBi product.

Table 4 shows the reactions for each of the two-phase reaction conditions tested, with refluxing at 80-90° C. and 0.1 eq AcCl fixed for all reactions. The equivalents of IPA, volume of n-heptane and reaction time were the variables screened. To recycle the unreacted HMBA, the aqueous phases from Entry 2b, 4a, 4b, 4c, 4d were combined and acidified with concentrated hydrochloric acid to adjust the pH to 2.0-2.5 forming two phases after pH adjustment. The top organic layer which contained the unreacted HMBA and a small amount of HMBi were separated and was then directly adapted to HMBi synthetic process as described above but without the drying step (Entry 5a, Table 4). All organic phases from reaction 2b, 4a-4d and 5a were combined and evaporated to give crude product.

TABLE 4

Lab-scale reactions conducted for the screening of two-phase reaction conditions for HMBi synthesis. AcCl (0.1 eq) were added to all reactions

| Entry | HMBA (g, dried or not) | IPA (g, eq to HMBA) | n-Heptane present during reaction (mL, vol to HMBA wt) | Reaction Time (h) | Remarks |
|---|---|---|---|---|---|
| 1a | 100, not dried | 220, 6.25 eq | 0 | 16 | one-phase reaction |
| 1b | 100, dried | 220, 6.25 eq | 0 | 16 | |
| 1c | 100, dried | 105.6, 3.0 eq | 0 | 16 | |
| 2a | 100, dried | 52.8, 1.5 eq | 200, 2 vol | 16 | Two-phase reaction |
| 2b | 100, dried | 70.4, 2.0 eq | 200, 2 vol | 16 | with Equivalents of |
| 2c | 100, dried | 88.0, 2.5 eq | 200, 2 vol | 16 | IPA |
| 2d | 100, dried | 105.6, 3.0 eq | 200, 2 vol | 16 | |
| 3a | 100, dried | 70.4, 2.0 eq | 300, 3 vol | 16 | Volumes of n- |
| 3b | 100, dried | 105.6, 3.0 eq | 300, 3 vol | 16 | heptane |
| 3c | 100, dried | 105.6, 3.0 eq | 400, 4 vol | 16 | Volumes of n- |
| 3d | 100, dried | 140.8, 4.0 eq | 400, 4 vol | 16 | heptane |
| 4a | 50, dried | 35.2, 2.0 eq | 100, 2 vol | 8 | Reaction time |
| 4b | 50, dried | 35.2, 2.0 eq | 100, 2 vol | 12 | |
| 4c | 50, dried | 35.2, 2.0 eq | 100, 2 vol | 16 | |
| 4d | 50, dried | 35.2, 2.0 eq | 100, 2 vol | 20 | Reaction time |
| 5a | Recycled (2b, 4a, 4b, 4c, 4d) | 35.2, 2.0 eq | 100, 2 vol | 16 | Recycle |

TABLE 5

Conversion rate of HMBi as affected by Equivalents of IPA, Volume of n-heptane and Reaction time

| Entry | Equivalents of IPA | Volume of n-Heptane present during reaction | Reaction Time (h) | Conversion rate (%) |
|---|---|---|---|---|
| 1a (one phase reaction) | 6.25 | 0 | 16 | 76.2 |
| 1b | 6.25 | | | 73.7 |
| 1c | 3.0 | | | 56.4 |
| 2a | 1.5 | 2 | 16 | 71.9 |
| 2b | 2.0 | | | 76.4 |
| 2c | 2.5 | | | 78.3 |
| 2d | 3.0 | | | 80.2 |
| 3a | 2.0 | 3 | 16 | 79.6 |
| 3b | 3.0 | 3 | | 81.9 |
| 3c | 3.0 | 4 | | 83.7 |
| 3d | 4.0 | 4 | | 86.8 |
| 4a | 2.0 | 2 | 8 | 77.2 |
| 4b | | | 12 | 76.7 |
| 4c | | | 16 | 76.3 |
| 4d | | | 20 | 77.4 |
| 5a | 2.0 | 2 | 16 | 75.2 |

Results: All conversion rates of HMBi from lab scale reactions are listed in Table 5. The number of equivalents of IPA and the volume of n-heptane were found improved the conversion rate. When 2 vol of n-heptane were used as solvent (Entry 2a-2d, Table 5), the conversion rate (71.9%, 76.4%, 78.3% and 80.2%) increased along with the equivalents of IPA (1.5, 2.0, 2.5 and 3.0 eq). When 3.0 eq of IPA was used (Entry 1c, 2d, 3b and 3c, Table 5), the conversion rate of HMBi (56.4%, 80.2%, 81.9% and 83.7%) increased along with the volume of n-heptane (0, 2, 3, and 4 vol). Similar trends were found when 2.0 eq of IPA were used for the reaction (Entry 2b and 3a, Table 5). Reaction time did not show much effect on the conversion rate as long as it was ≥8 h (Entry 4a-4d, Table 5).

Compared with one-phase processes, the conversion rate of HMBi was improved by two-phase reactions. One phase processes have a conversion rate of 76.2% (Entry 1a, Table 5), which decreases when HMBA was pre-dried with no n-heptane (73.7%, Entry 1b, 56.4%, Entry 1c, Table 5). It could be improved to 76.4-86.8% if ≥2.0 eq of IPA and ≥2 vol of n-heptane was used. HPLC analysis of final products.

The HPLC method used for the quantification of HMBA and HMBi is the method according to EURL Evaluation Report on the Analytical Methods submitted in connection with the Application for Authorisation of a Feed Additive according to Regulation (EC) No 1831/2003 (JRC.D.5/FSQ/CvH/SB/ag/Ares(2012)240861) adapted to our lab. The mobile phase contained 0.2% phosphoric acid (85%) in water (v/v, Channel A) and acetonitrile (Channel B). After washing and separating, 100 μL of the organic layer and the water layer were each dissolved in 10 mL acetonitrile respectively. And 10 μL of the sample was injected per assay. An optimum detection wavelength (210 nm) was chosen for simultaneous quantitation of these two molecules. The percentages of constituents were calculated by integration of peak areas.

Figure 5A:
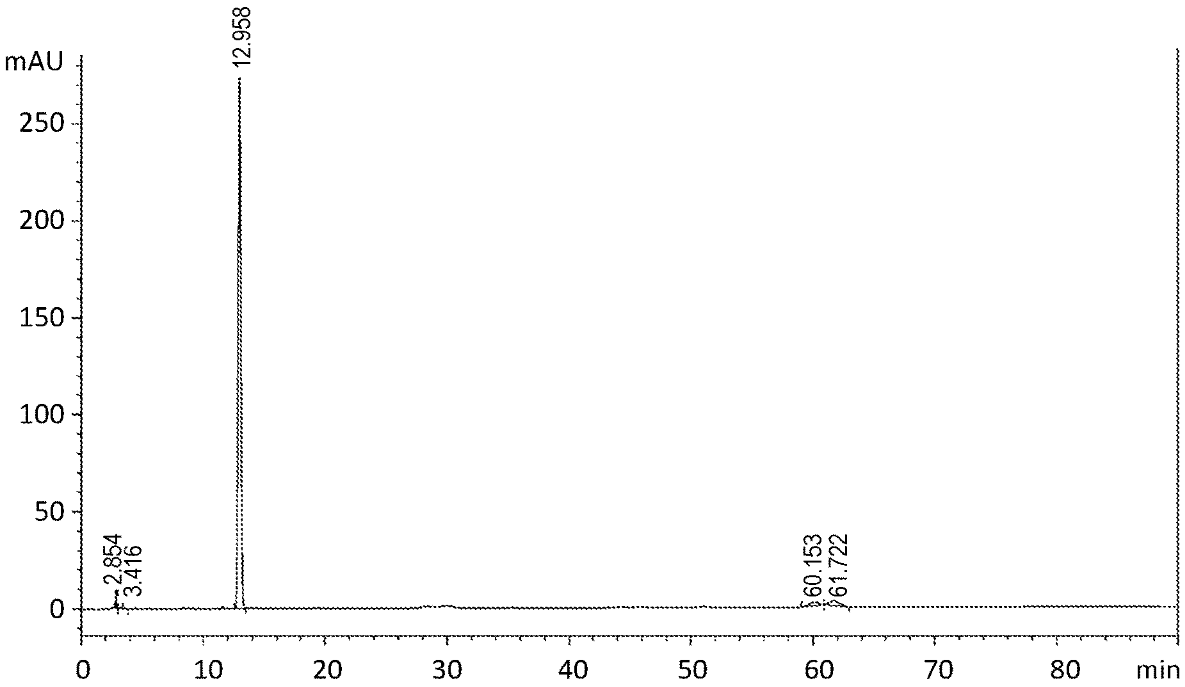
FIG. 5A is an HPLC chromatogram depicting the results for HPLC analysis of the products from an HMBi synthesis as disclosed in Example 13.
Figure 5B:
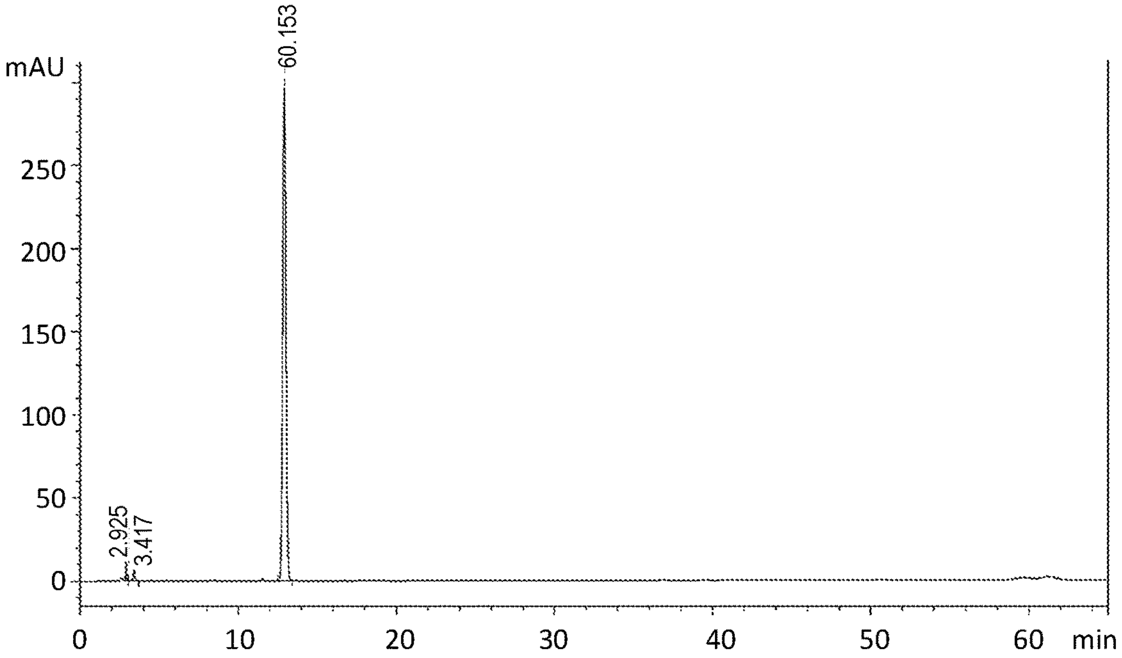
FIG. 5B is an HPLC chromatogram depicting the results for HPLC analysis of the products from an HMBi synthesis using a two-phase reaction as disclosed in Example 13.

Analysis of dimer and oligomer impurities: Dimer and oligomer impurities in the reaction mixture were reduced or eliminated by the two-phase reactions, as shown in FIGS. 5A (Table 5A) and 5B (Table 5B). The HPLC purity of the reaction mixture was improved from 92.8% to 97.9%.

TABLE 5A

| Peak # | Retention Time | Type | Peak Width | Peak Area | Peak Height | Peak Area |
|---|---|---|---|---|---|---|
| 1 | 2.854 | VV | 0.0589 | 40.2284 | 10.2272 | 0.9502 |
| 2 | 3.416 | VB | 0.1315 | 31.77293 | 3.44720 | 0.7505 |
| 3 | 12.958 | BB | 0.2265 | 3928.80005 | 271.98337 | 92.8018 |
| 4 | 60.153 | BB | 0.6506 | 93.02583 | 1.74597 | 2.1974 |
| 5 | 61.722 | BB | 0.6979 | 139.71103 | 2.44418 | 3.3001 |

TABLE 5B

| Peak # | Retention Time | Type | Peak Width | Peak Area | Peak Height | Peak Area |
|---|---|---|---|---|---|---|
| 1 | 2.925 | BV | 0.0568 | 41.57926 | 11.33293 | 0.9624 |
| 2 | 3.417 | VB | 0.1079 | 47.69163 | 6.55052 | 1.1039 |
| 3 | 12.938 | BB | 0.2221 | 4230.94189 | 297.16232 | 97.9336 |

Example 14. Pilot Scale Reaction of HMBi with Acetyl Chloride (AcCl) and Isopropanol Using a Two-Phase Reaction Two 1500 L glass-lined reactors, one 3000 L stainless steel reactor and one 3000 L stainless steel storage tank were used. Briefly, 600 kg HMBA (88% HMBA and 12% water) and 1200 L (820.8 kg) n-heptane were charged into the 3000 L reactor and heated to 90° C. to allow n-heptane to be distilled out. The distilled n-heptane was settled in another 3000 L storage tank for 3 hours. An aqueous layer formed at the bottom which was 49-55 kg water. The residue HMBA was then equally divided into two portions, each of which was transferred to one 1500 L glass-lined reactor respectively. To each 1500 L reactor was added HMBA (300 kg), IPA (2.5 eq/264 kg for the $1^{st}$ batch, 1.5 eq/158.4 kg for the following batches that used recycled solvent), n-heptane (2 vol, 600 L, 410.4 kg, using fresh for the $1^{st}$ batch and recycled for following batches), and AcCl (0.1 eq, 15.0 kg). The mixture was heated to 80-90° C. and refluxed for 10-12 h, then cooled to 40-50° C., followed by the addition of NaOH solution (20% wt/wt) to adjust pH to 8-9. The organic layer and aqueous layer became transparent afterwards. Both layers were sampled for the analysis of HMBA and HMBi contents. The conversion rate was calculated by dividing total HMBi amount from each of the organic and aqueous layers by theoretical HMBi output. The aqueous layer was back extracted with two portions of n-heptane (0.5 vol each, 102.6 kg). All organic phases were combined and washed with small amount of water (60 L), which were then concentrated in the 3000 L stainless steel reactor to give crude HMBi product.

A total of 4 batches were prepared including one recycling batch. For the recycling batch, aqueous phases from previous 3 batches were combined and acidified with concentrated sulfuric acid to bring down the pH to 2.0-2.5. Phase separation was observed. The top organic layer which contained about 265 kg HMBA and small amount of HMBi were separated. It was then directly adapted to HMBi synthetic process as described above but without the drying step. Reaction conditions for all 3 batches and one recycling batch are listed in Table 6.

TABLE 6

Reaction conditions for 3 pilot batches and 1 recycle batch production of HMBi. Other reaction parameters were the same if not mentioned in this table.

| Batch | HMBA (kg) | n-Heptane (L, vol) | Fresh or recycled | IPA (kg, eq) |
|---|---|---|---|---|
| 1 | 600 | 1200, 2 vol | Fresh | 528.0, 2.5 eq |
| 2 | 600 | 1200, 2 vol | Recycled | 316.8, 1.5 eq |
| 3 | 600 | 1200, 2 vol | Recycled | 316.8, 1.5 eq |
| 4 | Recycled | 600, 2 vol | Recycled | 158.4, 1.5 eq |

Results: Conversion rates and adjusted yields of HMBi from pilot scale synthesis are listed in Table 7. The conversion rates were very close to those from lab scale synthesis if the same reaction conditions were employed, indicating the process was scalable. A total of 1823.5 kg crude HMBi product was obtained from 1800 kg HMBA for an overall adjusted yield of 81.5%. Assays for crude products were all over 90%.

TABLE 7

Conversion rates and isolated yields of HMBi from pilot scale synthesis

| | | | Crude HMBI Product | | |
|---|---|---|---|---|---|
| Batch | HMBA (kg) | Conversion rate (%) | Quantity (kg) | Assay (%) | Adjusted yield* (%) |
| 1 | 600 | 77.2 | 511.4 | 90.1 | 68.2 |
| 2 | 600 | 75.6 | 513.5 | 90.2 | 68.6 |
| 3 | 600 | 77.7 | 515.8 | 89.8 | 68.6 |
| 4 | Recycled | | 282.8 | 93.9 | |
| All Combined | 1800 | | 1823.5 | | 81.5 |

*Adjusted yield (%) = (Quantity of crude product (kg) × Assay (%))/Theoretical yield of HMBI (kg)

Figure 6:
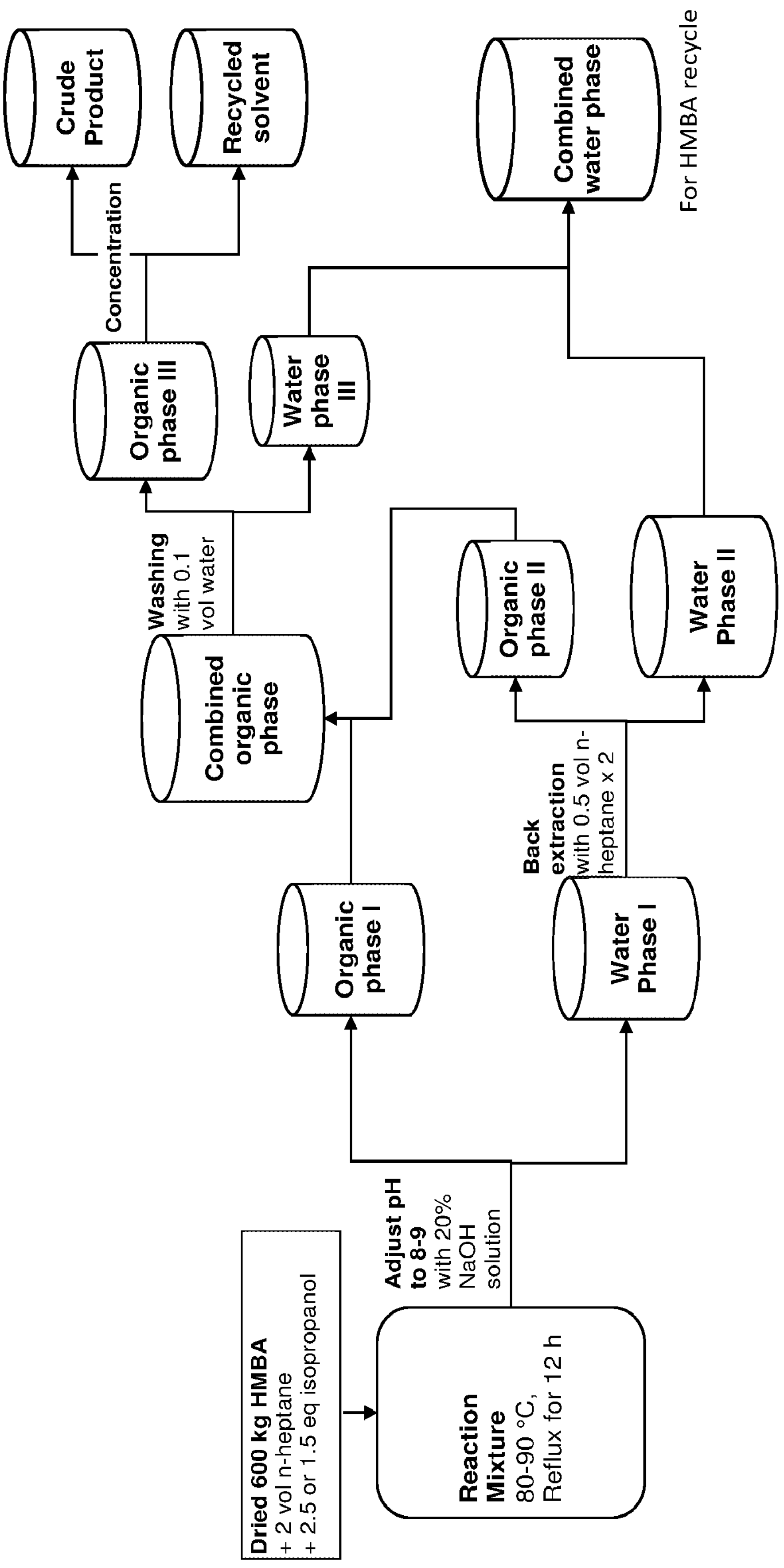
FIG. 6 is an example process flowchart for the synthesis of HMBi using a two-phase reaction as disclosed herein.

FIG. 6 shows an example process flowchart for the synthesis of HMBi using a two-phase reaction.

The invention claimed is:

1. A method of preparing a compound of Formula (I):

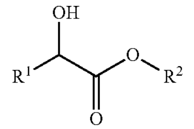

(I)

wherein $R^1$ is chosen from H; $C_{1-4}$ alkyl optionally substituted with —OH, —SH, —S—$C_{1-4}$ alkyl, —$CONH_2$, —$NR^aR^b$, or guanidino; phenyl optionally substituted with —OH or $C_{1-4}$ alkyl; indolyl; and imidazolyl;

wherein $R^a$ and $R^b$ are each independently H or $C_{1-4}$ alkyl; and $R^2$ is $C_{1-8}$ alkyl or $C_{4-7}$ cycloalkyl;

comprising a) reacting at room temperature a compound of formula $R^xC(O)Cl$ with a compound of formula $R^2OH$ to form a reagent of Formula (A):

(A)

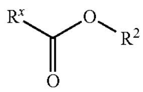

and to form in-situ an acid catalyst;

wherein $R^x$ is chosen from H, $C_{1-4}$ alkyl, and $CH_2$—CH—; and b) reacting, at a temperature of 80° C. to 90° C., a compound of Formula (II):

(II)

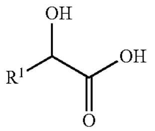

with the reagent of Formula (A) in the presence of the in-situ generated acid catalyst.

2. The method of claim 1, wherein the reagent of Formula (A) serves as a reaction solvent.

3. The method of claim 1, wherein $R^1$ is $C_{1-4}$alkyl optionally substituted with —OH, —SH, —S—$C_{1-4}$ alkyl, —$CONH_2$, —$NR^aR^b$, or guanidino, or wherein $R^1$ is $C_{1-4}$alkyl optionally substituted with —OH, —SH, or —S—$C_{1-4}$ alkyl.

4. The method of claim 1, wherein $R^1$ is —$CH_2CH_2$—S—$CH_3$ and $R^2$ is isopropyl.

5. A method of preparing a compound of Formula (I-A):

(I-A)

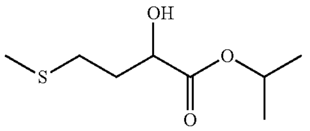

comprising reacting acetyl chloride with isopropyl alcohol to form isopropyl acetate; and reacting a compound of Formula (II-A):

(II-A)

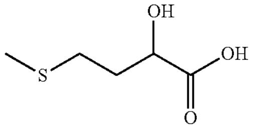

with isopropyl acetate.

6. The method of claim 1, wherein the method further comprises adding at least one nonpolar solvent to the reaction between the compound of Formula (II) and Formula (A).

7. The method of claim 6, wherein the method is a two-phase reaction comprising a hydrophobic phase and a hydrophilic phase of a reaction mixture.

8. The method of claim 6, wherein the at least one nonpolar solvent is chosen from petroleum ether, toluene, methyl tert-butyl ether, hexane, cyclohexane, hexanes, n-heptane, octane, nonane, decane and benzene.

9. The method of claim 6, wherein the nonpolar solvent is n-heptane.

10. The method of claim 1, wherein the compound of Formula (II) is present in a sample comprising water prior to the reacting, and the method further comprises reducing the amount of water in the sample by contacting the sample with an acid chloride of Formula (D):

$C_{1-3}$ alkyl—C(O)Cl (D)

to generate in situ a catalyst mixture comprising HCl, and combining the reagent of Formula (A) with the catalyst mixture.

11. The method of claim 1, wherein the compound of Formula (II) is present in a sample comprising water prior to the reacting, and the method comprises treating the sample with a drying agent prior to the reacting.

12. The method of claim 11, wherein the at least one drying agent is an azeotrope solvent chosen from hexane, n-heptane, n-propanol, isopropyl acetate, ethyl acetate, toluene and benzene.

13. The method of claim 1, wherein the reacting provides a reaction mixture comprising the compound of Formula (I), and the method further comprises removing the reagent of Formula (A), by distillation to provide a crude residue, adding base to the crude residue, where the base is sodium acetate, aqueous NaOH, aqueous $NaHCO_3$, aqueous $K_2CO_3$, or aqueous $Na_3PO_4$, to increase the pH to a range from about 5 to about 8 to provide a basic mixture, and extracting the compound of Formula (I) from the basic mixture into at least one nonpolar solvent to provide an extract.

14. The method of claim 13, comprising removing the at least one nonpolar solvent from the extract, optionally by distillation, to provide the compound of Formula (I) in at least about 95% purity by GC, HPLC, or by weight.

15. The method of claim 1, wherein the reacting in step b) is performed for a time ranging from about 1 hour to about 24 hours, or from about 2 hours to about 15 hours, or from about 3 hours to about 14 hours, or from about 4 hours to about 12 hours, or from about 4 hours to about 10 hours, or about 10 to about 20 hours, or about 14 to about 16 hours.

16. The method of claim 1, wherein the method further comprises combining isopropyl alcohol with acetyl chloride to produce a solution of isopropyl acetate in isopropanol and the reacting of the compound of Formula (II) with the reagent of Formula (A), wherein the reagent of Formula (A) is isopropyl acetate, comprises adding the compound of Formula (II) to the solution of isopropyl acetate in isopropanol.

17. The method of claim 1, wherein the reacting provides a crude compound of Formula (I) that has a purity by weight, GC, and/or HPLC of at least about 95%, or at least about 96%, or at least about 97%, or at least about 98%, wherein the crude compound of Formula (I) has not been further purified.

18. The method of claim 1, wherein the reacting provides a crude compound of Formula (I) that comprises less than about 5% by weight, or less than about 3%, by weight, of dimeric and/or oligomeric compounds, wherein the crude compound of Formula (I) has not been further purified.

* * * * *